United States Patent
Blackburn et al.

(10) Patent No.: US 11,288,308 B2
(45) Date of Patent: *Mar. 29, 2022

(54) SYSTEM FOR A VERIFIABLE PHYSICAL OBJECT WITH A DIGITAL REPRESENTATION AND RELATED APPLICATIONS

(71) Applicant: Scientia Potentia Est., LLC., Charleston, SC (US)

(72) Inventors: Jeremy Blackburn, Charleston, SC (US); Justin Southward, Charleston, SC (US); W. Kurt Taylor, N. Charleston, SC (US); Karl David, Charleston, SC (US); Austi Critchfield, Clearwater, FL (US); Michael Lu, N. Charleston, SC (US); Tim McVicker, Charleston, SC (US)

(73) Assignee: Scientia Potentia Est., LLC, Charleston, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/176,056

(22) Filed: Feb. 15, 2021

(65) Prior Publication Data

US 2021/0165822 A1 Jun. 3, 2021

Related U.S. Application Data

(63) Continuation-in-part of application No. 16/997,840, filed on Aug. 19, 2020, which is a
(Continued)

(51) Int. Cl.
*G06F 16/583* (2019.01)
*G06F 16/58* (2019.01)
(Continued)

(52) U.S. Cl.
CPC .......... *G06F 16/5854* (2019.01); *G06F 16/51* (2019.01); *G06F 16/5866* (2019.01); *G06K 9/00201* (2013.01)

(58) Field of Classification Search
CPC .. G06F 16/5854; G06F 16/51; G06F 16/5866; G06K 9/00201; G06K 9/0063;
(Continued)

(56) References Cited

U.S. PATENT DOCUMENTS

| 1,059,298 A | 4/1913 | Hoyne |
| 7,031,930 B2 | 4/2006 | Freeman et al. |

(Continued)

FOREIGN PATENT DOCUMENTS

| EP | 3617824 A1 | 4/2020 |
| WO | 2018163044 | 9/2018 |
| WO | 2018177568 | 10/2018 |

OTHER PUBLICATIONS

Hughes, Dave, The Impact of Blockchain Technology on the Construction Industry:, Feb. 19, 2017; medium.com, 8 pages. (Year: 2017).

(Continued)

*Primary Examiner* — Garcia Ade
(74) *Attorney, Agent, or Firm* — Kim and Lahey Law Firm, LLC; Douglas W. Kim

(57) ABSTRACT

This computerized system can include a computer system in communication with an immutable storage; a first data capture device and a second data capture device can be in communications with the computer system; a set of computer readable instructions can be included in the computer system configured for receiving a first event record including a first location, a first time and a first set of metadata wherein the first set of metadata includes an original digital representation captured by the first data capture device of the
(Continued)

physical object, receiving a subsequent event record from the second data capture device and, determining if the original digital representation is equivalent to the subsequent digital representation thereby providing for verification that the same physical object transitioned from an originating event to a subsequent event.

20 Claims, 27 Drawing Sheets

Related U.S. Application Data continuation-in-part of application No. 16/994,585, filed on Aug. 15, 2020, now Pat. No. 11,232,652, which is a continuation-in-part of application No. 16/991,916, filed on Aug. 12, 2020, now Pat. No. 11,216,823, which is a continuation-in-part of application No. 16/876,080, filed on May 17, 2020, which is a continuation-in-part of application No. 16/810,782, filed on Mar. 5, 2020, now Pat. No. 11,216,781, which is a continuation-in-part of application No. 16/510,642, filed on Jul. 12, 2019, now Pat. No. 11,216,772, which is a continuation-in-part of application No. 16/452,076, filed on Jun. 25, 2019, said application No. 16/810,782 is a continuation-in-part of application No. 16/510,634, filed on Jul. 12, 2019, now Pat. No. 10,713,737, which is a continuation-in-part of application No. 16/452,076, filed on Jun. 25, 2019, said application No. 16/810,782 is a continuation-in-part of application No. 16/452,076, filed on Jun. 25, 2019.

(51) Int. Cl.
  *G06F 16/51* (2019.01)
  *G06K 9/00* (2022.01)
(58) Field of Classification Search
  CPC ............ G06K 9/00771; G06K 9/00288; B64C 39/024; B64C 2201/127; G06Q 10/1057; G06Q 40/08; G06Q 50/08; G06Q 10/103; G06Q 10/0875; G06Q 10/109; G06Q 40/125; G06Q 50/265; G16H 40/20; H04N 9/8205; H04N 5/77
  USPC .......................................................... 382/305
  See application file for complete search history.

(56) References Cited

U.S. PATENT DOCUMENTS

| | | |
|---|---|---|
| 7,330,821 B2 | 2/2008 | Wares |
| 7,508,973 B2 | 3/2009 | Okabe et al. |
| 7,546,576 B2 | 6/2009 | Egli |
| 7,602,288 B2 | 10/2009 | Broussard |
| 7,898,403 B2 | 3/2011 | Ritter et al. |
| 8,004,397 B2 | 8/2011 | Forrest et al. |
| 8,103,596 B1 | 1/2012 | McFarlin et al. |
| 8,321,302 B2 | 11/2012 | Bauer et al. |
| 8,428,904 B2 | 4/2013 | Vock et al. |
| 8,521,620 B2 | 8/2013 | Livingston et al. |
| 9,135,787 B1 | 9/2015 | Russell et al. |
| 9,727,923 B2 | 8/2017 | Teh et al. |
| 10,121,112 B1 | 11/2018 | Vasquez, Jr. et al. |
| 10,338,913 B2 * | 7/2019 | Franchitti .............. G06N 5/022 |
| 2006/0137015 A1 | 6/2006 | Fahrny et al. |
| 2007/0220342 A1 | 9/2007 | Vieira et al. |
| 2010/0058364 A1 | 3/2010 | Sherrill et al. |
| 2011/0060659 A1 | 3/2011 | King et al. |
| 2017/0031676 A1 * | 2/2017 | Cecchetti .................. H04L 9/12 |
| 2017/0286572 A1 | 10/2017 | Hershey et al. |
| 2018/0210436 A1 | 7/2018 | Burd et al. |
| 2019/0251575 A1 | 8/2019 | Berti et al. |
| 2019/0287181 A1 | 9/2019 | Lekas |
| 2019/0317935 A1 | 10/2019 | Berti et al. |
| 2019/0333169 A1 | 10/2019 | Povar et al. |
| 2019/0377904 A1 | 12/2019 | Sinha et al. |
| 2020/0034766 A1 | 1/2020 | Borges |

OTHER PUBLICATIONS

Penzes, Balint, "Blockchain Technology in the Construction Industry: Digital Transformation for High Productivity", Dec. 2018; Ice: Institution of Civil Engineers, 52 pages. (Year: 2018).

Miskins, Carlos, "Digitizing the Construction Sector Using Digital Twin Technology Simulations", Dec. 2018, https://www.challenge.org/insights/digital-twin-in-construction/, 8 Pages.

Verma, Urvashi, "What Are Digital Twins in Smart Buildings?", Oct. 31, 2018, https://inbuildingtech.com/bms/digital-twin-commercial-office-building/, 9 Pages.

Ghanem, Amine et al., "A Case Study for Improving Construction Project Management", 51st ASC Annual International Conference Proceedings, 9 pages (Year: 2015).

Barista, David, "'BIM for all' platform pays off for contractor", https://www.bdcnetwork.com/bim-aH-platform-pays-contractor, Aug. 13, 2020; 12 pages.

* cited by examiner

SYSTEM FOR A VERIFIABLE PHYSICAL OBJECT WITH A DIGITAL REPRESENTATION AND RELATED APPLICATIONS

RELATED APPLICATIONS

This application is a continuation in part of U.S. application Ser. No. 16/997,840 filed Aug. 19, 2020, which is a continuation in part of U.S. patent application Ser. No. 16/994,585 filed Aug. 15, 2020 entitled "System For Management Of Verification Of Project Commencement and Completion", which in turn is a continuation in part of U.S. patent application Ser. No. 16/991,916 entitled "System For Management Of Warranty Information For Projects And Materials", filed on Aug. 12, 2020 which in turn is a continuation in part of U.S. patent application Ser. No. 16/876,080 entitled "Digital Asset System For Management Of Projects And Materials", filed May 17, 2020 which in turn is a continuation in part of U.S. patent application Ser. No. 16/810,782, entitled "System For Management And Verification of Code Compliance", filed on Mar. 5, 2020 which in turn is a continuation in part of U.S. patent application Ser. No. 16/410,634, entitled "Use of A Persistent Storage Reference Construction Metadata and to Use Smart Contracts for a Project or process", filed on Jul. 12, 2019, U.S. patent application Ser. No. 16/510,642 entitled "Use of a Blockchain-Based Distributed Ledger and Smart Contracts for a Project or process", filed on Jul. 12, 2019 both of which are continuations of U.S. patent application Ser. No. 16/452,076, entitled "Site Super System For Project locations", filed Jun. 25, 2019 which all are incorporated reference.

BACKGROUND

1) Field of the System

A system for pairing a physical object with a digital representation providing for a verifiable link between the physical object with its virtual representation during a process that can include a first event and a second event occurring over a period of time.

2) Background

In the modern economy, there is a continuing trend for digitization. This trend includes attempts to create digital representations of physical objects so that the physical objects can be represented. Historical, digitization focused on creating a digital representation of a physical object so that the digital information can be manipulated by information systems and stored on a database. For example, a bank balance can be the digital representation of the fiat currency that is in the possession of the bank account holder. While these systems are sufficient for fungible objects such as currency, there is a challenge when the object is not fungible and needs to be tracked. For example, during the manufacturing of a good, components for that good can be specific to that good and are not readily substituted between different goods. In the manufacturing of a vehicle of different makes, models, and years, one type of part cannot necessarily be substituted for a different part as the part that is needed is dependent upon the vehicle being manufactured. Therefore, traditional methods of tracking parts such as UPC and other barcodes are not sufficient. The UPC, for example, does not necessarily capture the changes to the part from year to year. This disadvantage is evidence when a replacement part is needed and while the UPC is the same, the actual part is not compatible with the good needing the part.

Using existing technology taken from industries such as the financial industry does not solve the problem as they cannot verifiably pair a digital representation with a physical object. In the financial industry, digitization begins with electronic information representing the dollar value of an account and not a specific physical dollar itself. As the financial industry progressed, the electronic current itself became the asset as discussed in U.S. Pat. No. 9,135,787, this patent discloses a Bitcoin kiosk/ATM that facilitates the buying or selling of Bitcoin. The underlying technology for Bitcoin is blockchain. Blockchain alone cannot verifiably pair a digital representation with a physical object because there is no linkage between the physical object and the digital asset under the Bitcoin scheme alone. Blockchain provides immutability, rather than the ability to pair physical objects with digital representation.

This type of digitization where the digital information represents the asset that is to be distinguished with electronic scanning of a physical assets. Electronic scanning simply creates a digital copy that is separate from the physical object and becomes an independent object itself. Despite the illegality of this example, the digital scan of US currency and the US currency itself are not equivalent. The US currency can be spent without reference or modification of the digital scan and the digital scan can be manipulated without reference or modifications to the US currency. The physical and the digital are not verifiably paired. The inability to pair the digital representation with physical object makes traditional digitization of physical objects challenging as the digital object and the virtual representation are not functional equivalents and therefore are not verifiably paired.

Further, there is a significant disadvantage with current systems in that the current systems have the potential for rehypothecation. Hypothecation means pledging an asset as collateral for a debt so that in the event of a default, the asset can be seized (e.g., foreclosure or repossession) to satisfy the default at least partially on the debt. Rehypothecation is when the creditor uses the collateral from a first loan (e.g., original loan) and also uses it as collateral for a second loan. Rehypothecation increases uncertainty and adds risk in that actual ownership, lien, or collateral can become uncertain. If the collateral is only represented in physical form the risk of rehypothecation remains.

The ability to track object during a process can be improved when the object is properly and verifiable paired with a digital representation. In many industries, the systematic and logical workflow of physical objects increases the success of any project, process, activity, or providing a service. Generally, the creation or manufacturing of a good can include a designer that can specify materials, suppliers that can supply materials, that workers that may need a specific set of credentials, licenses or experience, and inspectors that can verify the delivery and performance of the goods and the manufacturing processes.

Currently, there is a lack of accountability, verification and reliability between physical objects and digital representations. The inability to verify the pairing of physical objects with digital representations negatively impacts current processes, increases risks, and increases costs in general. While there have been some attempts to add item information to a physical material, such as U.S. Pat. No. 8,321,302, these attempts have focused on tracking inventory levels and do not include verifiably pairing a physical object with a virtual representation. Further, these prior attempts focus on the identifier and not the physical object itself. Therefore, there is no assurance that the identifier remains associated with the physical object. This disadvantage can be seen in U.S. Pat. No. 8,521,620 which specifically states that if a RFID tag is lost or damaged, the system allows a user to enter an item number or style and tags of similar items are displayed, a new tag is generated and associated with the item having the lost or damaged tag. The ability to change RFID tags expressly shows that the physical object is not paired with the digital representation.

There have also been attempts to use inspection to assist with monitoring physical objects during a process. There have been attempts to provide for automated inspection such as U.S. Pat. No. 7,508,973 which discloses method of inspecting detects includes assigning a plurality of sets of image acquisition conditions, executing inspection using each of the sets of conditions, classifying all detected defects into real defects and false defects by use of an automatic defect classification function, and selecting, from the plurality of sets of conditions, a set of conditions ideal for detection. However, this attempt is reduced to a snapshot in time in the products lifecycle. This attempt does not pair the physical object to a digital representation nor does it provide for an audit trail throughout the process.

There have been some attempts to improve tracking of articles such as shown in U.S. Pat. No. 7,898,403 that are directed to a method and system for detecting construction equipment process failures. A database is populated from information from a third-party source and a process failure report is provided for processes that are outside a norm assigned to the construction equipment asset. U.S. Pat. No. 7,031,930 is directed to a method and system for managing complex projects or processes by monitoring subcontractors in real time, against a system after commencement of the project. U.S. Pat. No. 8,004,397 is directed to a mountable reporting source comprising a controller coupled with an interrogating component configured for automatically receiving an identifier which is unique to an asset having a position determining component. U.S. Pat. No. 8,428,904 discloses product integrity tracking system, shipping label and associated method. This patent is directed to label body for attaching to a product to be shipped or to packaging containing the product.

These systems do not verifiably pair a physical object with a virtual representation during the life of a project or process and do not account for the physical goods being detached from the "tag". The inability to verify that a digital representation is paired with the physical object prevents the use of digital wallets since a digital wallet does not include such as pairing. Previous attempts to verify such transactions fail to pair a physical object with a digital representation, disadvantages that can be seen in United States Patent Application Publication 2019/0303919.

It would be an advantage to have a system that can verifiably pair physical objects with virtual representations so that information systems can be used to track physical objects with reduced or eliminated risks that the digital representation no longer represents the original physical object.

It would be advantageous to have a system that can provide for multi-party verification of the pairing of a physical asset with a virtual representation for tracking of the physical asset and the associated project.

SUMMARY OF THE SYSTEM

In accordance with an exemplary embodiment, computerized system for verifiably pairing a physical object with a digital representation can be provided and can include a computer system in communication with an immutable storage; a first data capture device in communications with the computer system; a second data capture device in communications with the computer system; a set of computer readable instructions included in the computer system configured for: receiving a first event record ($E_1$) from the first data capture device including a first location ($L_1$), a first time ($T_1$) and a first set of metadata ($M_1$) wherein the first set of metadata includes an original digital representation captured by the first data capture device of the physical object, receiving a subsequent event record ($E_2$) from the second data capture device including a second location ($L_2$), a second time ($T_2$) temporally subsequent to the first time and a second set of metadata ($M_2$) wherein the second set of metadata includes a subsequent digital representation captured by the second data capture device of the physical object, and, determining if the original digital representation is equivalent to the subsequent digital representation thereby providing for verification that the same physical object transitioned from an originating event to a subsequent event.

The set of computer readable instructions can include instructions for determining if a similarity between the original digital representation and the subsequent digital representation is within a predetermine range. The first data capture device can be remote from the computer system. The subsequent event record can include a verification data representing that verification of the physical object subject to the subsequent event is the same physical object associated with the originating event according to the first event record. The set of computer readable instructions can include storing the first event record on the immutable storage and the set of computer readable instructions for determining if the first digital representation is equivalent to the subsequent digital representation includes retrieving the first event record from the immutable storage. The subsequent event record can include a verification data representing that an individual viewed the metadata of the first event record and compared it with the physical object. The second set of metadata is taken from sources from the group consisting of public records, enterprise software, computer device or any combination thereof.

The computerized system can include a computer system in communication with an immutable storage; a set of computer readable instructions included in the computer system configured for: retrieving a first event record ($E_1$) from the immutable storage wherein the first event record includes first location ($L_1$), a first time ($T_1$) and a first set of metadata ($M_1$) wherein the first set of metadata includes a first digital representation captured by a first data capture device of the physical object, retrieving a subsequent event record ($E_2$) from the immutable storage including a second location ($L_2$), a second time ($T_2$) temporally subsequent to the first time and a second set of metadata ($M_2$) wherein the second set of metadata includes a subsequent digital representation captured by a second data capture device of the physical object, and, determining if a similarity exists between the original digital representation and the subsequent digital representation is within a predetermine range.

The set of computer readable instructions can include instructions for determining if the physical object is the same physical object represented by the first digital representation during an occurrence of a second event. The subsequent event record can include a verification data representing that verification of the physical object subject to the subsequent event is the same physical object associated with the first event. The subsequent event record can include a verification data representing that an individual viewed the metadata of the first event record and compared it with the physical object. The first data capture device can be a remote from the computer system and the second data capture device.

The system can include for verifiably pairing a physical object with a digital representation comprising: a computer system in communication with an immutable storage; a data capture device in communications with the computer system; a set of computer readable instructions included in the computer system configured for: retrieving a first event record ($E_1$) from the immutable storage wherein the first event record includes a first location ($L_1$), a first time ($T_1$) and a first set of metadata ($M_1$) wherein the first set of metadata includes a first digital representation captured by a first data capture device of the physical object, creating a subsequent event record ($E_2$) from the data capture device including a second location ($L_2$), a second time ($T_2$) temporally subsequent to the first time and a second set of metadata ($M_2$) wherein the second set of metadata includes a second digital representation captured by the data capture device of the physical object, and, determining if a similarity between the first digital representation and the second digital representation exists.

The computer readable instructions can include instruction for determining if the similarity is within a predetermine range. The computer readable instruction can include instructions for determining if a similarity between the first digital representation and the second digital representation exists includes retrieving the first event record from the immutable storage. The subsequent event record includes a verification data representing that verification of the physical object subject to the subsequent event is the same physical object associated with the first event according to the first event record. The data capture device can be a first data capture device; and, the computer readable instruction can include instructions for determining if a similarity between the first digital representation and the second digital representation exists includes retrieving a first image of the physical object, comparing the image to a second image captured by a second data capture device and determining if the images represent the same physical object. The instructions can determine if a similarity between the first digital representation and the second digital representation exists includes capturing an object indicium affixed to the physical object, comparing the indicium on the object at the subsequent event to a digital indicium included in the first event record. The subsequent event record can include a verification data representing that an individual viewed the object indicium and compared it with the digital indicium retrieved from the immutable storage and included in the first event record.

In one embodiment, the system can provide a hashed event record where the event record can include metadata associated with a capture device as well as indicium associated with the physical object and store the record on a blockchain platform including the platforms associated with Bitcoin, Ethereum and the like.

DETAILED DESCRIPTION

The present system provides for verified pairing of a physical object with a virtual representation.

Figure 1A:
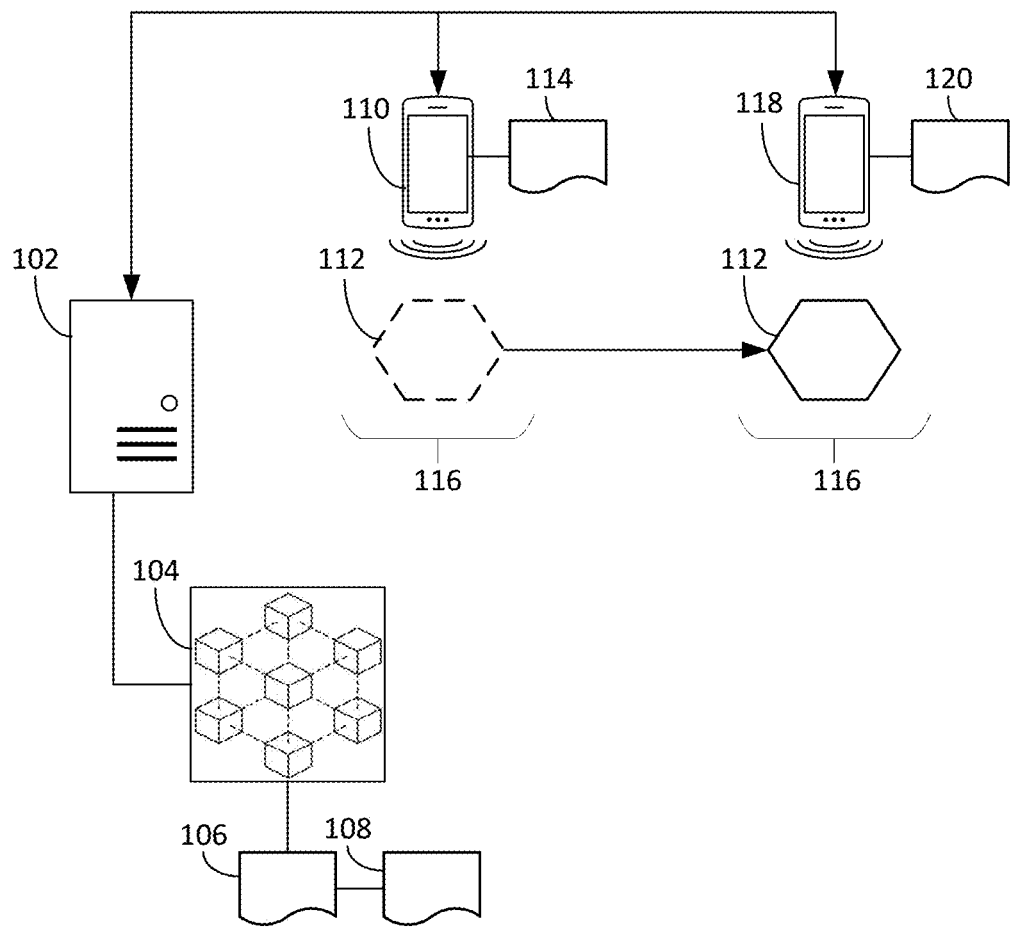
FIG. 1A is a diagram of aspects of the invention.
Figure 1B:
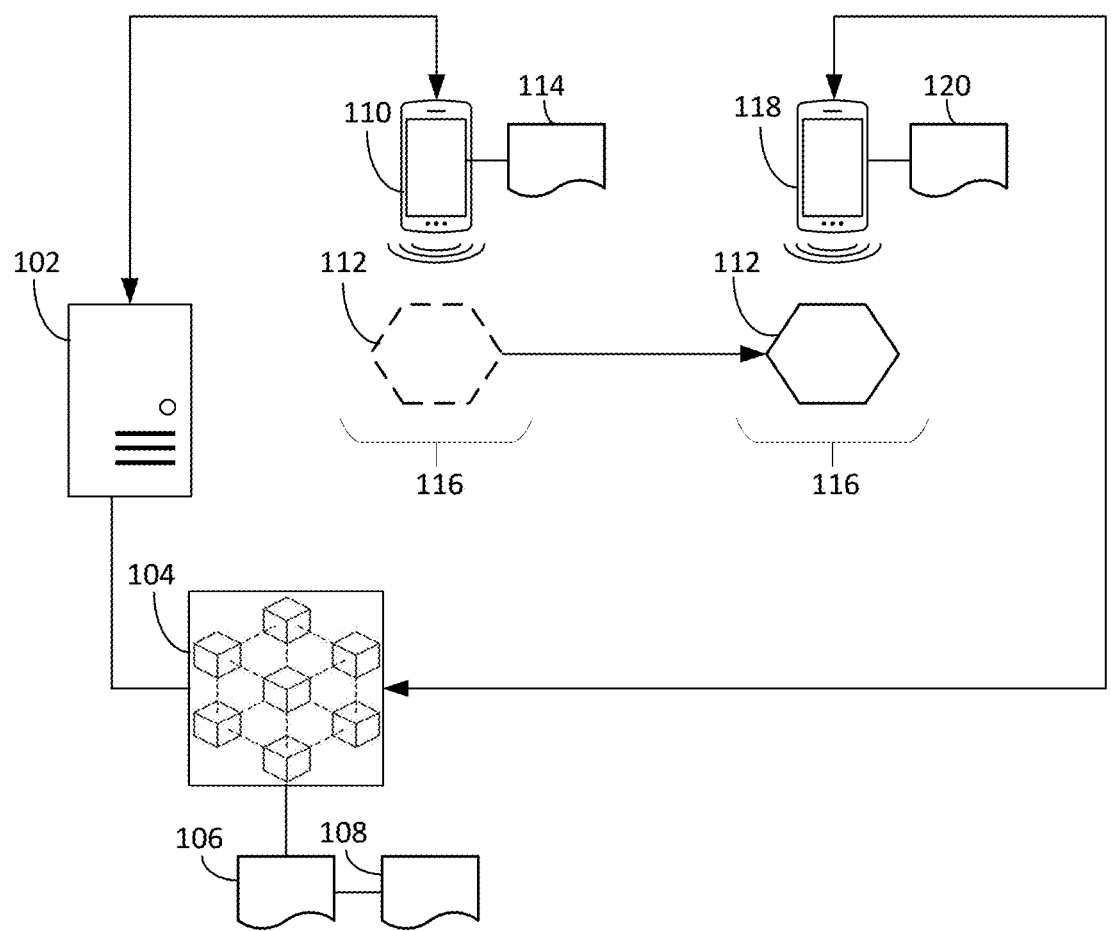
FIG. 1B is a diagram of aspects of the invention.

Referring to FIG. 1A illustrates a computer system 102 can be in communications with a data storage system 104. The data storage system can be permanent, immutable and persistent so that the information stored on the data system, once storage, cannot be changed. The data system can include a plurality of computer systems where data can be copies onto each computer system. When using the data storage system, the data can be static so that once created and stored, it cannot be changed. Examples of data storage platforms include hard drives, solid state drives, tapes, and cloud storage systems. The immutable data storage system can use blockchain, crypto-shredding, WORM, append only, distributed ledger technology, immutable cloud storage, immutable record retention (e.g., Oracle Cloud Infrastructure Object Storage, and any combination thereof. In one embodiment the immutability is accomplished by the data storage system only allowing records to be appended to the storage media without the ability to modify the record one written. One such system includes blockchain. When a first record 106 is written to the data storage system, the record cannot be changed. When a second record 108 is written to the data storage system, it is stored later in time to the first record thereby effectively providing a chronologically trail of events associated with the physical object and digital representation.

In one embodiment, the first record can be associated with a first event and a second record can be associated with a second event. The order the first record and the second record are written on the immutable storage can be used to show that some period of time elapsed between the first record and the second record. This functionality can add to the verification process as attempts to improperly tamper with the immutable storage may be discovered when the first record and the second record are not in chronological order. Further attempts to improperly tamper with the immutable storage can be discovered when the metadata of the first record and the second record are inconsistent with the first record and the second record being stored chronologically.

The first event record can be associated with a first event and the second event record can be associated with a second event. The data associated with these events can be retrieved from the capture device and used in creating and writing the associated event record. If the date and time setting of the data capture device are incorrect, this discrepancy can be identified by comparison with the event record created and compared to related records in the immutable storage. In one embodiment, metadata integrity used by the system can be designed to identify inconsistencies with date and time. For example, a drone can be used to capture one or more images from a project, such as construction roof project, and the drone may experience date and time inaccuracies so that the date and time in its metadata is in error. The error can be identified by comparing the irregular time of the drone and the hash/block time of the metadata that was committed to the persistent storage layer. The difference can be with a range that results in an alert being sent to a user. This alert allows the users to remedy the error, repair the device (e.g., drone) and mitigate risk of date and time, and other inconsistencies, in the future.

The first event can differ from the second event by time, activity, process, location, or any combination.

In one embodiment, metadata associated with the event and event record and a ledger hash time, representing when the event record is stored (e.g., committed) to the immutable storage can be used to validate the metadata provided from the data capture device. If the data capture device has an incorrect time, a comparison of the ledger hash time with the metadata from the data capture device can identify an error. Identifying an error can be used to alert users to data capture device issues and can indicate that the data capture device needs to be serviced or replaced prior to its next use.

The metadata that can be associated with the capture device can include weather conditions, which can include a sun angle, which can be compared with environmental weather conditions to approximate the data capture time. Metadata associated with an image of video can be used to verify weather conditions in the image or video. Time and location metadata can be retrieved from publicly sources or remote sources and captured with the device metadata to determine of the captured weather in the image or video is the same as being reported locally on that day and at that time.

In one example, drone can be the capture device and images, or video captured from the drone of a physical object such as a roof can show repairs that occur over time. In the event that the drone footage was disputed, metadata that can include location, date and time and comparing weather visible in drone footage to reported weather conditions to add verification to the drone metadata. In one example, data associated with a worker, such as a vehicle, license plate, of other indicia can be captured by the drone. For example, if a license plate can be captured, the license plate information can be compared with public data and the attendance of the worker at a location or physical object can be verified.

The metadata that is captured can be dependent upon the device and can include metadata associated with a worker, equipment, weather, enterprise software, security hardware and software, material, indicia, smart contracts, public records, authentication information, date, time, location, entity and any combination of these examples. The biometric data may include facial recognition, an iris/retinal scan, a fingerprint scan, a hand scan, a voice print, or heart rate signature and any combination.

In one embodiment, an image or video captured can be used to identify an approximate time where data was captured by the data capture device. The metadata associated with the data capture can include weather conditions, sun angle, which can be compared with environmental weather conditions to approximate the data capture time. In one embodiment, the data capture can include the location so that the location of the data capture device can be used to retrieve environmental weather conditions when the data capture occurs.

The data capture device can capture data in response to an event associated with the physical object. For example, if the physical object changes location, is modified, transferred, integrated, or other action, process or procedure associated with the physical object can signify an event.

A location can include a manufacturing place, construction site, business providing services (e.g., vehicle repair service), origination site, delivery site or other location where the materials will be used including the creation, maintenance, repair or integration into an assembly.

Verification, including verification of an event, can include verifying that the physical object and the virtual representation match and can be accomplished in a variation of methods including interaction with identification elements such as a tag, label, and the like, capturing an image of the material, capturing a video of the material, capturing indicia such as a tag physically affixed or otherwise associated with the material, human visual inspection, and any combination. Identification of an individual performing or otherwise associated with an event can be captured by identification devices (e.g., cards, tags, RF ID) and biometrics including visual capture (e.g., facial recognition), voice recognition, iris scan, fingerprint, palm print, weight, dimensions, change in weight, dimensions or other attributes, and any combination. Examples of verification processes can include having stored data about the physical object and comparing the physical object with the date, using machine learning process video, using imagery, audio clips and other media to and any combination. Individuals Human inspectors can be used to verify physical objects and events onsite and offsite. Individuals can process video, imagery, audio clips and other media to verify assets and events and provide the verification to the system at one or more events. Upon verification of an event, smart contracts can be executed according to verification of the physical object and event.

In operation, a first data capture device 110 can be in communications with the computer system 102 so that data captured by the first data capture device can be transmitted to the computer system. The first data capture device can have a first capture device metadata 114 originating from the data device that can be included in the first record 106. The first data capture device can also capture object data associated with the physical object. Object data can include an image of the physical object, tag, label, RFID, weight, dimensions, and other indicia and any combination thereof. The object data can be captured at a first event 116 that can include a change in state of the physical object, change in location change in time or any combination thereof. When an event occurs, which can be a second event, a second data capture device 118 can have a second capture device metadata 120 originating from the data device that can be included in the second record 108. The second data capture device can also capture object data associated with the physical object 112 at the second event 120.

The first capture device metadata and object data can be used to create the first record which can be a first event record. The first event record can be stored on the immutable storage. The second capture device metadata and object data captured by the second data capture device can be used to create the second record which can be a second event record. The second event record can be stored on the immutable storage.

During data capture by the first data capture device, object indicia can be capture where the object indicia is associated with the object. The object indicia can include a still image of the object, a label affixed to the object, a radio frequency identification (RFID) tag, an ultra-high frequency (UHF) tag, a bar code, a QR code, a Bluetooth beacons, alpha-numeric characters, and any combination thereof. The object indicia can be included in the first event record and stored on the immutable storage. When a change in time, location or other event occurs the second data capture device can capture the object indicia. Once captured, the object indicia can be compared to the object indicia in the first event record and if the two matches, then verification exists that the physical object associated with the second event is the same physical object that was present at the first event. In one embodiment, the second capture device can capture data, transmit the data to the computer system 102 and computer readable instructions on the computer system can perform the comparison of the object indicia capture as the second event with the object indicia included in the first event record.

Referring to FIG. 2B, the second data capture device can be in communications with the immutable storage. Computer readable instructions on the second data capture device can capture the object data at the second event, retrieve the first event record, compare the object indicia from the second capture device with the object indicia of the first event record and determine if the physical at the second event is the same physical object at the first event. In one embodiment, the second data capture device can store a second event record that can include object indicia capture at the second event on the immutable storage. The computer system can be notified that a second event record has been stored. The computer system can retrieve the first event record and the second event record and compare the respective object indica to determine of the physical object is the same physical object at the first event and the second event. If the object indicium is not the same, a notification can be provided indicating that the physical object has been changed, modified or otherwise different between the first event and the second event.

Figure 1C:
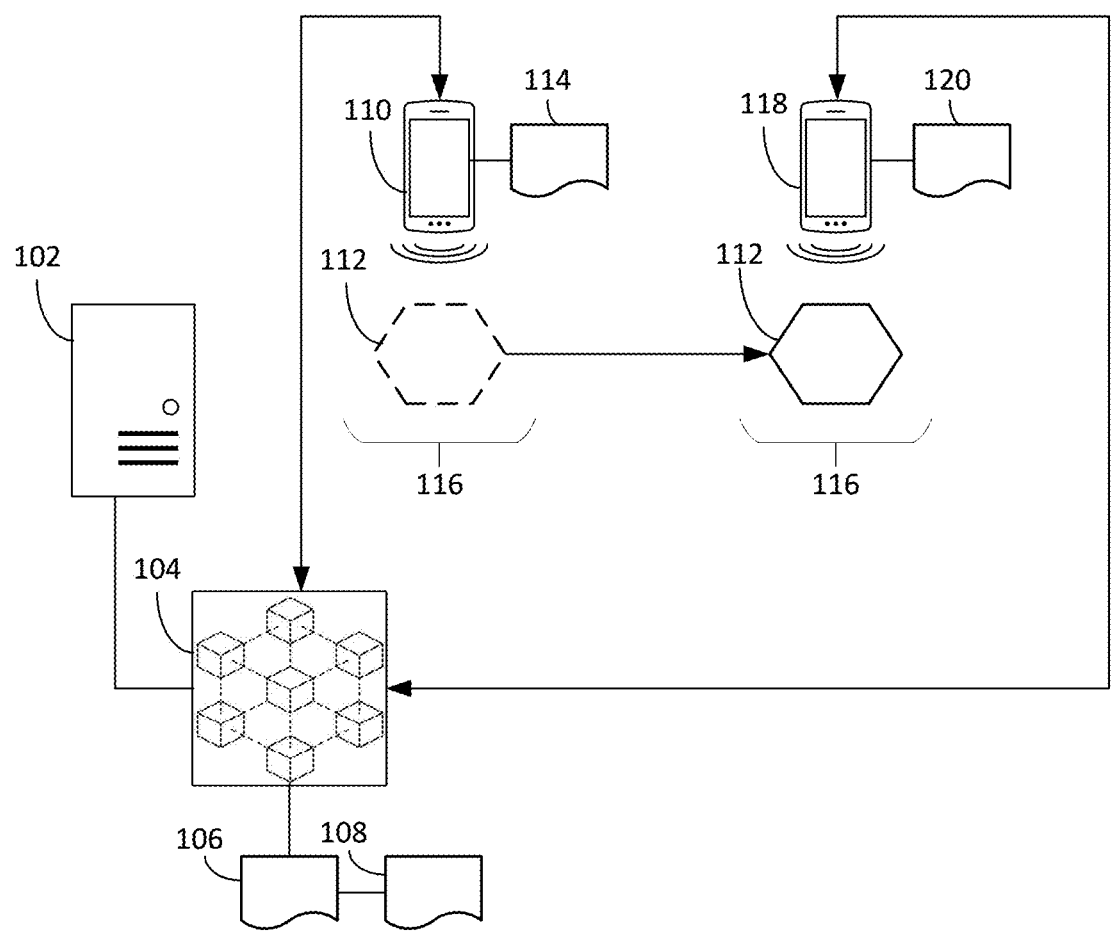
FIG. 1C is a diagram of aspects of the invention.

Referring to FIG. 1C, the first data capture device can be in communication with the immutable storage. In one embodiment, the first data capture device can capture data at a first event that can include object indicia, create a first event record, and store the first event record on the immutable storage. The second data capture device can retrieve the first record having the object indicia from the immutable storage and compare the object indicia captured by the second data capture device with the object indicia of the retrieved first event record.

The first data capture device and the second data capture device can be the same device.

The system can therefore pair the physical object with a digital representation, such as an object indicium, and verify among events that physical object has not been improperly changed. This system can provide for verifications at each event that the physical object has not been replaced, modified, or otherwise changes.

Figure 2:
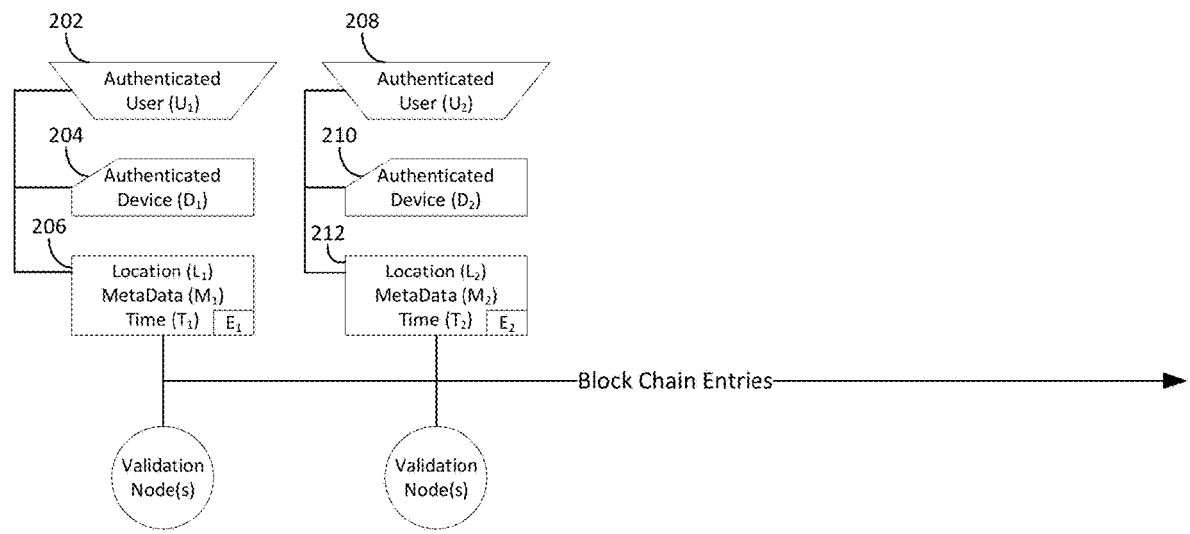
FIG. 2 is a diagram of aspects of the invention.

Referring to FIG. 2, one embodiment the user of a data capture device can be verified at 202 so that the user can be authorized to use the data capture device or to perform data capture at the first event. The data capture device can be authenticated at 204 representing the data capture device is the correct data capture device and is in working order. The metadata that can be captured by the data capture device can include a location, a time and additional metadata shown as 206. The user can be a first user and in one embodiment a second user of a data capture device can be verified at 208 so that the user can be authorized to use the data capture device or to perform data capture at the first event. A second data capture device can be authenticated at 210 representing the data capture device is the correct data capture device and is in working order. The metadata that can be captured by the data capture device can include a location, a time and additional metadata shown as 212. In one embodiment, the first event record and the second event record can be committed to immutable storage such as blockchain using validation nodes included in the immutable storage structure.

Figure 3:
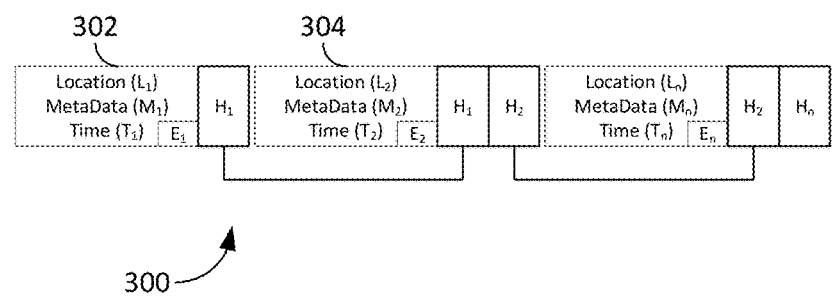
FIG. 3 is a diagram of aspects of the invention.

Referring to FIG. 3, in one embodiment the second event record 44 can be linked to the first event record 302 to create a digital audit trail 300 that includes object indicia verifying that the physical object remains the same physical object throughout a process or where the physical object was modified, changed or otherwise different during the process.

One example of the invention can include when a material is selected for transport by the supplier, a shipping company can be sent a shipping order representing the material to be transported, an origin and destination. The shipping order can be provided directly to the shipping company or can be retrieved from the immutable storage. Once the shipping company receives the shipping order, it can travel to the origin and receive the material which can represent a first event, and capture data associated with the first event. A first event record can be created representing that the shipping company received the materials and pair the received material with object indicia. In one embodiment, verification that the material is associated with the object indicia can be performed by an individual receiving the material.

Once that material is delivered to the destination, the shipping company can unload the material, a second event, a second verification can occur verify that the material that was delivered to the destination was the same material received at the origin. A second event record can be created representing that the material was delivered and that the material matches the material at the origin and described on the shipping order. The second event record can include the environmental conditions when the material was delivered, delivery notes and the like. The destination can be a receiving entity that can create a third event record representing that the material ordered was received. The receiving entity can use a third data capture device to capture the object indicia and create a third event record. The computer system second data capture device and third capture device can verify that the delivered material matches the ordered material, and that the material has not been modified, changed, substituted, or otherwise different from the origin to the destination.

The receiving entity can use a data capture device that can include biometrics or other indicia to verify that workers using the material are authorized and have the necessary licenses, work certifications, experience, authorizations [other examples?] as well as for verified payroll and insurance coverage. The verification can be through biometric identification devices such as a camera or other image capture device, facial recognition, voice recognition, retinal scans, fingerprint scanners, hand scanners, and other biometric devices. In one embodiment, the computing logic may allow authorized individuals to manually enter the presence of another authorized individual, including on the controller at the project location or through a remote device that can be determined to be at the project location, within a boundary associated with the project location, in proximity to the system. In one embodiment, individuals may be verified and paired with a virtual representation using two-factor authentication.

The receiving entity can be uniquely associated with a location. A location marker can be affixed at the receiving entity and uniquely identify the receiving entity and in one embodiment, a project location. The location marker can be read by a data capture device and provided to the computer system and the immutable storage. In one embodiment, the receiving entity can receive metadata such as a shipping identifier associated with the delivery, including a truck, trailer, pallet, or other container so that the materials are known to be received at the project location.

The computer system can be contained in a housing such as a kiosk and can be physically associated with a project location. The project location can be defined by a boundary representing the perimeter of the physical location. The system can include a sensor and reader which can be selected from the group consisting of radio frequency identification (RFID) detector, ultra-high frequency (UHF) detector, a bar code scanner, a QR code scanner, near frequency communication (NFC) device; Bluetooth beacons, an optical character recognition (OCR) device and any combination thereof. An environmental sensor, such as a weather sensor or weather station, can be in communications with the or included in the housing and configured to record the weather and other environmental conditions at the location and at different times during the project. If the environmental sensor detects a change in the environmental condition, it can represent an event.

The system may record the date and time of events such as the arrival and departure of materials, individuals, workers, supplies, third parties, inspections, and the like to and from the project location, the date and time associated with environmental conditions including weather. The environmental conditions can be used to modify the schedule for workers so that workers are not working during inclement weather, tasks are not preformed outside specified environmental conditions, and materials are delivered and installed during specified environmental conditions.

The system may track the movement of material at a project location or during a process or to and from the project location thereby creating an audit trail associated with the material. Scanning technology such as RFID readers, UHF readers and/or the like may be utilized to assist the location tracking for tools, equipment, materials and even workers. The tracking the material assists with reducing the risk of loss, theft, mis-delivery, and the like. For example, the tracking solution may indicate instances of possible theft, such as when the materials are leaving the project location when the removal of the materials is not proper.

The system may allow for the establishment of one or more geofenced zone that can be associated with delivery areas, worker entrance exit areas, task areas, storage areas, assembly areas, distribution areas and any combination thereof. These areas could be monitored and established with access allowances or restrictions to control movement of material, individuals and equipment to assist with the prevention of loss, mistakes, inefficiencies, and damage. The system can assist with verification that materials stored-on locations are consistent with specifications associated with the materials. A first event can be the material being deposited at a location in a first zone and a second event can be the material being deposited at a second zone. The first event can be associated with the object at a first zone and a second event can be associated with the object in the same zone, at a later time.

The system can also use smart contracts associated with events and stored on the immutable storage that can be self-executing upon satisfaction and verification of contractual terms and objects associated with an event. For example, when an object is delivered from a shipper to the receiving entity and the receiving entity verifies that the object was properly delivered, a smart contact that instigates payment to the shipper can be performed.

Figure 4B:
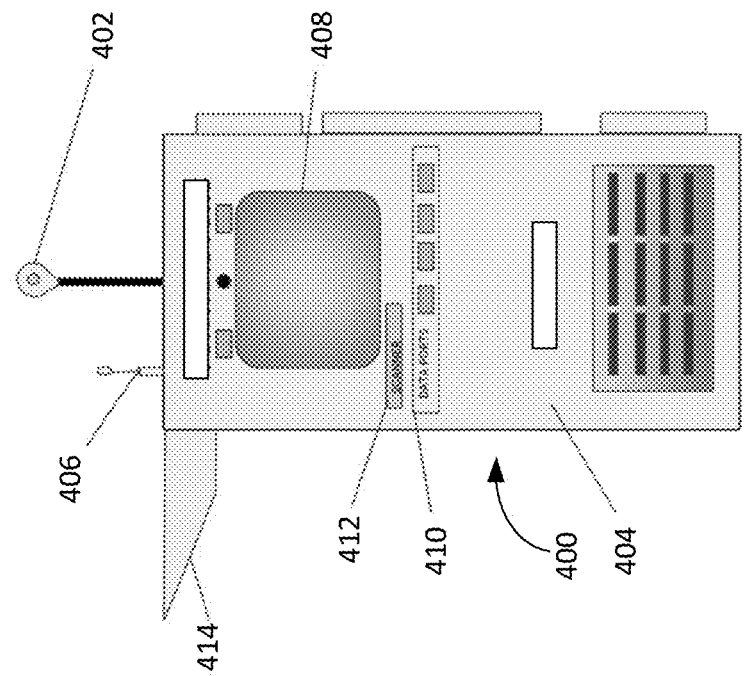
FIG. 4B is a schematic of aspects of the invention.
Figure 4A:
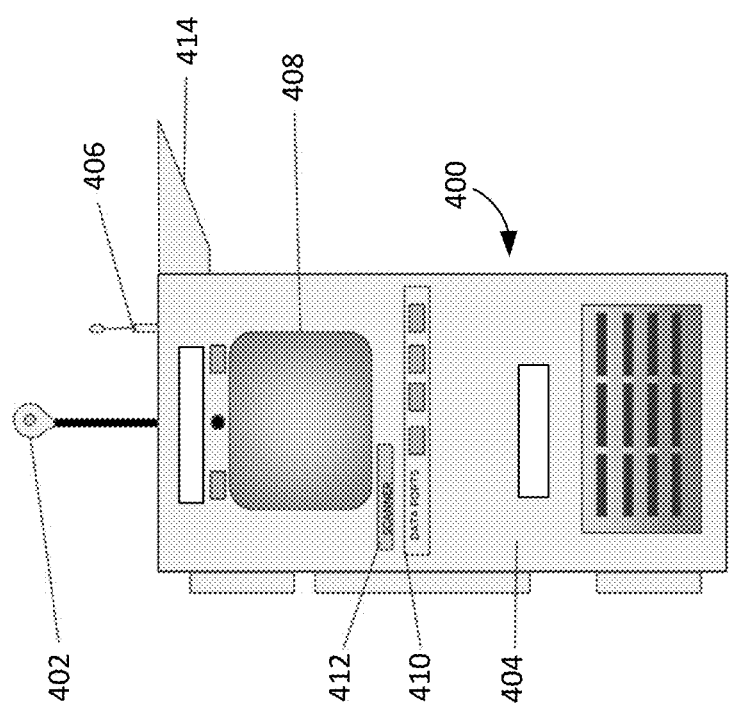
FIG. 4A is a schematic of aspects of the invention.

Referring to FIG. 4A, in one embodiment the computer system can be contained in a housing 404 can be physically associated with the project location, virtually associated with the project location or both. A unique location marker can be disposed at the project location to uniquely identify the project location. For examples, a transmitter such as a RFID can be associated with the project location by embedding it is a permanent fixture such as a concrete slab, foundation, structure, and the like. The system can read the information from the location marker and associate its actual location with the project location. The location marker can include an alpha, numeric, or graphical information such as a number, letters, barcodes, QR code, physical or geographic coordinates (e.g., GPS coordinates), passive transmitter, active transmitter and the like. Each system can have a unique identifier and each project location can have a unique identifier. The deliveries may utilize various scanning and reader technology such as scanner 412.

A first side of the system 400 can include a camera 402 for obtaining images of materials, equipment, individuals, or other items entering or leaving the project location as well as images of individuals along a perimeter. The camera 402 may capture biometric images upon which biometric recognition may be performed. Multiple cameras may be placed on or around the housing. The cameras may have biometric recognition and motion detection capabilities. System 400 may include an addition to the camera 402 or instead of the camera 402, biometric-based identification devices that may be used to confirm the identity of individuals entering, leaving or on the perimeter of the project location. The system 400 may include an antenna 406 for communicating with a network including a wireless network, Wi-Fi network, Bluetooth, quantum networks, cellular network (e.g., 4G or 5G network) and any combination. The system 400 may include a housing 404 made of suitable weather resistant material, appropriately sealed to protect the internal hardware. The system 400 may include a display 408, such as a touchscreen display, upon which information may be displayed and entered. The display 408 may include an integrated camera that may be used to capture images and that may be used in performing facial recognition of individuals. The display may also include or operatively associate with one or more integrated speakers for providing audio output, a microphone for receiving audio information to facilitate two-way communications to a remote location. The system 400 may include a scanner 412 for scanning items, such as deliveries, as will be explained in more detail below. The scanner 412 may be, for example, a QR scanner, an Optical Character Recognition (OCR) or a bar code scanner 412 in some instances. The side of the system 400 shown in FIG. 4A can be used for deliveries and inspections. A delivery person may scan delivered materials, equipment, or other items via the scanner 412 and may interface with the system using the touch screen display 408. An inspector may scan or take images of inspection documents via the scanner 412 or camera and may interface with the system using the touch screen display 408. In some embodiments, there may be fewer sides in which to interact with the system for all authorized personnel. An overhang 414 may be provided to assist in decreasing glare and protecting some of the items on the housing from the weather.

FIG. 4B depicts a side of the system 400. This side can include a touch screen display 408 as well as a scanner 412. Display 408 may include or be operatively associated with an integrated camera for capturing images, speakers for providing audio output and a microphone to facilitate two-way communications with a remote location. Still further, this side of the system 100 may include data ports 410. The system 400 may be accessed to gain access to equipment, tools and to sign in or sign out when leaving or entering the project location, as will be described below.

Figure 4D:
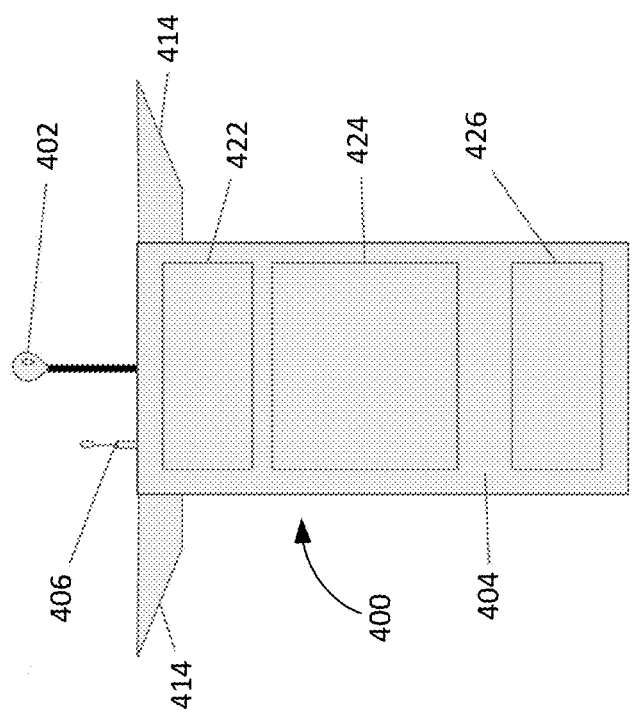
FIG. 4D is a schematic of aspects of the invention.
Figure 4C:
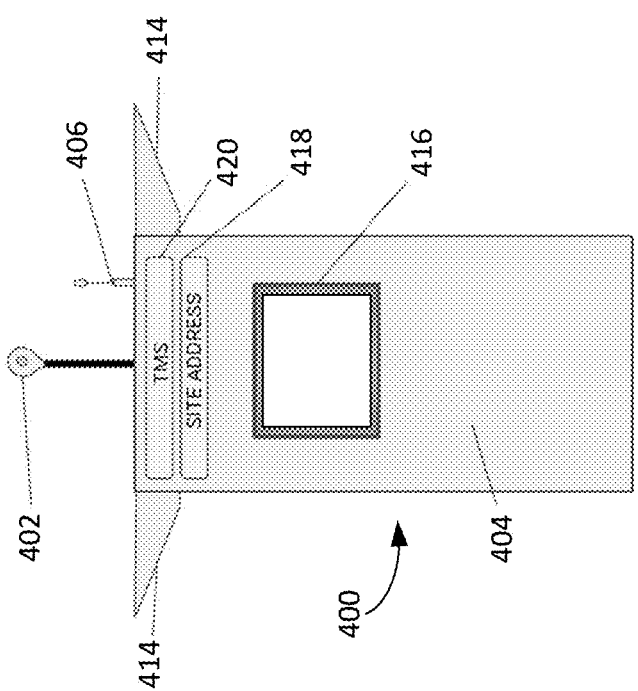
FIG. 4C is a schematic of aspects of the invention.

FIG. 4C shows a third side of the system 400. This side has a location 416 in which information such as permits, specifications, instructions, tax information, plans, and the like and may be displayed. In some embodiments, the information displayed may assume electronic form so that a video display is provided in the area 416 of the housing 404. A tax map submap (TMS) number 420 for the project location may be displayed on the housing 404. Other location identifying information can be displayed such as location number, store number, assembly number, area within the project location and the like. In addition, the site address 418 may be displayed on the system 400. The site address may refer to both the mailing address for the project location and/or other physically identifying information associated with the location.

FIG. 4D shows a side of the system 400. An access panel 422 may be provided to access a breaker box for the system 400. An additional access panel 424 may also be provided to access internal components of the system 400. Still further, access panel 426 may be provided to gain access to power source for providing power at the project location. The access panel 426 may be under programmatic control in some instances to regulate access to the power source. If access is granted, the panel is unlocked, whereas if access is denied, the access panel 426 is locked. In some embodiments, access to the power supply may be controlled by controlling the flow of power to the power source under programmatic control from the controller. These control mechanisms may be used separately or in conjunction.

Figure 6:
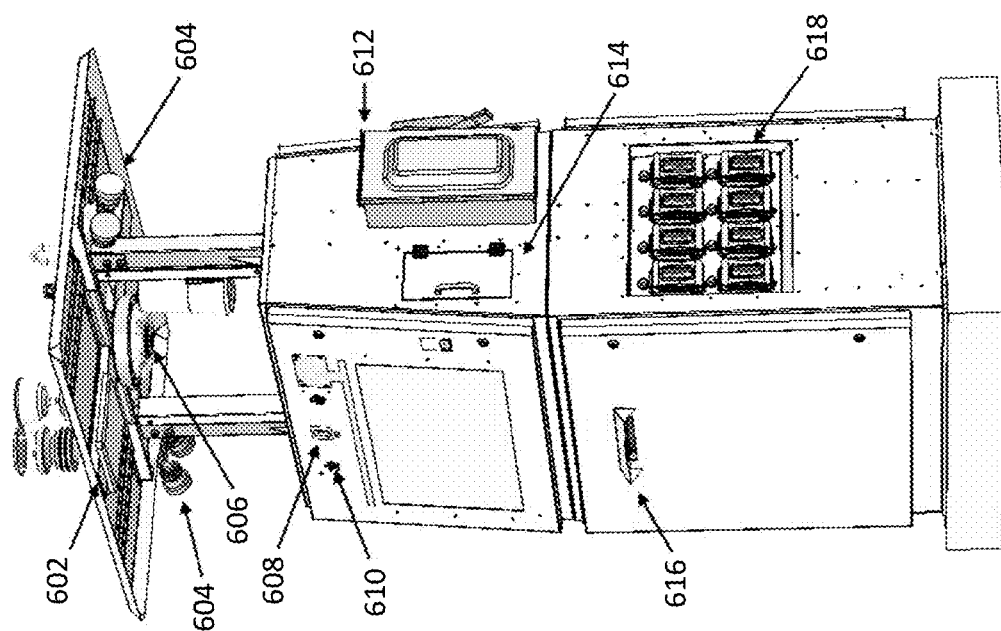
FIG. 6 is a schematic of aspects of the invention.
Figure 5:
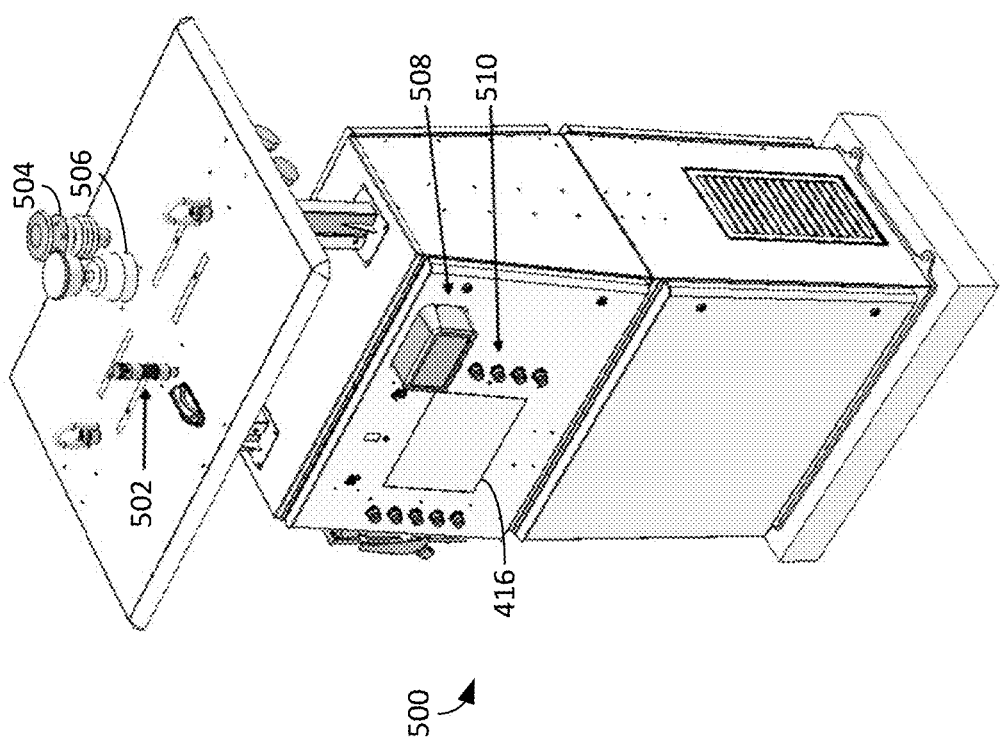
FIG. 5 is a schematic of aspects of the invention.

Referring to FIGS. 5 and 6, the housing 500 can include a worker side that is configured to be used by a worker at the project location. The housing can include an alarm indicator 502 that can be actuated as described herein. The housing can include a weather station 504 that can include an integrated or separate fluid (e.g., rain) collector 506. Biometric reader 508 can include an iris scanner, fingerprint scanner, palm print scanner, facial scanner, or some combination. Display 416 can be proximity to input assemblies such as buttons 510. The housing can include a field receiver 602, lights 604 and camera 606. One or more cameras can provide a 360° field of view and include a wireless connection for transmitting images to a remote computer device. The images can also be used for input to the system including input allowing the system to identify delivered materials. The system can include one or more second cameras 608 such as webcams disposed at various locations around the system for capturing images. The lights can include motion activation and photoelectric activation. Speakers 610 can be included to provide audio information to a user, worker, inspector, or other party using or near the system. The audio information can include instructions, alarms, and the like. Power junction 612 can include a shut off switch that can be used in emergency and non-emergency situations. The system can include a secondary power source, such as a battery, so that when the main power is shut off, an alarm can sound, notification send to a remote computer device of other indication that the system or power source has been powered down. The system can include a hand scanner (not shown) that can be protected by a hand scanner access door 614. A document scanner 616 can be included in the system for receiving physical documents, converting the physical document into a digital representation, and storing the digital representation on the computer readable medium or the immutable storage. The system or housing can include electrical outlets 618 for providing power to various tools and equipment at the project location including recharging batteries. The system can include a wired connection to remote computer devices of a transceiver to provide a wireless connection to remote computer devices.

Figure 7:
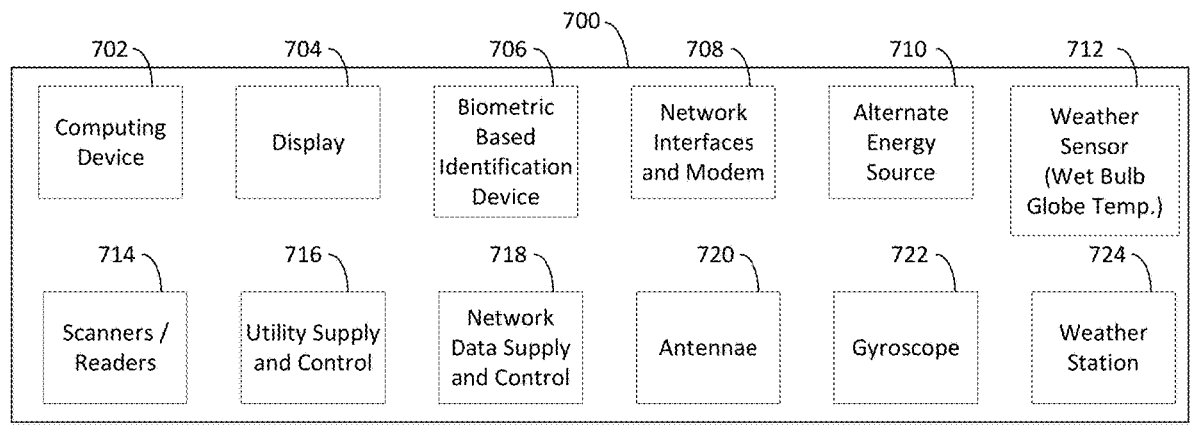
FIG. 7 is a schematic of aspects of the invention.

FIG. 7 depicts components that may be included in the system of exemplary embodiments even when not included in a housing. The system may include a computing device 702. The computing device 702 may take many different forms indicating a desktop computing device, a laptop computing device, a mobile computing device, an embedded system, a smartphone, special computer device, custom computer device, or the like. A display 704 may be integrated with the computing device 702 or as a separate device, such as a liquid crystal display (LCD) device, a light emitting diode (LED) display device or other types of display devices on which computer information may be displayed. One or more biometric-based identification devices 706 may be provided. As will be explained in more detail below, multiple biometric-based identification devices may be used. Network interfaces and a modem 708 may be provided. The network interfaces may interface the computing device 702 with a local area network or a wide area network wherein the networks may be wired or wireless. A modem may be provided to communicate telephonically or over cable lines with remote computing devices.

The system 700 may include various scanners and readers 714, such as those described above relative to housing. The system 700 may include a utility supply and control 716 and a mechanism for turning the utilities, such as power, gas and/or water, on and off under a programmatic control. The system 700 may include an internet data supply control 718 and a mechanism for turning the access to this service on and off under a programmatic control. Programmatic control may be provided to grant or deny access to such resources. The system 700 may include an antenna 720 for wireless communications signals to receive and transmit. The system 700 may include a gyroscope 722 to monitor any moving of the system. The gyroscope 722 may indicate motion indicative of whether someone is trying to move or tilt the housing or other component of the system. Logic may be provided to send a notification in such an event where the gyroscope indicates substantial enough movement. The system 700 may include a weather station 724 to measure current weather conditions, such as temperature, air movement, humidity, precipitation, barometric pressure, direct sunlight, and the like. Input from the weather station 724 may be used to inform decision making by the system in some instances. Alternatively, the weather may be collected via software, such as from a weather service or other weather source. Similarly, the system 700 may include a weather sensor 712. The sensor can be a wet bulb globe temperature adapted to measure, among other things, heat stress in direct sunlight, which accounts for temperature, humidity, air movement (direction and speed), sun angle and cloud cover (solar radiation).

Figure 8:
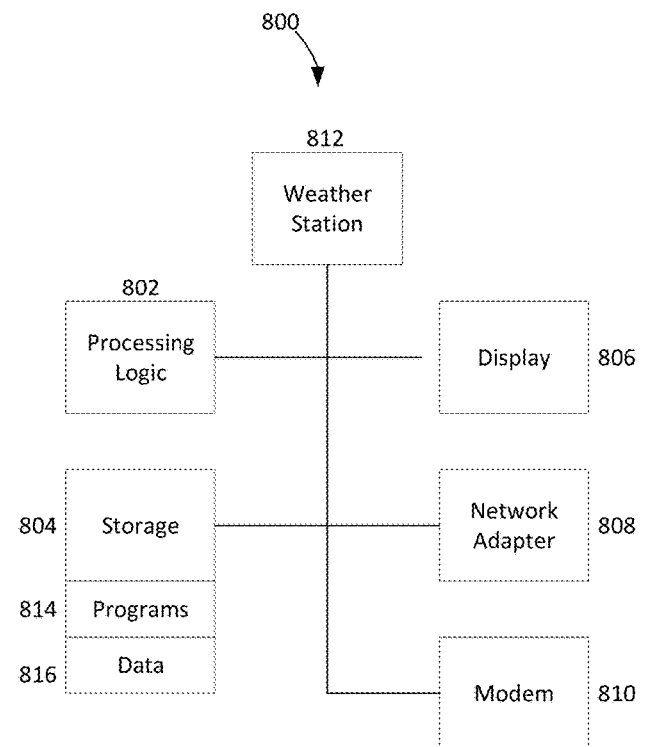
FIG. 8 is a schematic of aspects of the invention.

FIG. 8 shows an example of a computing device 800 for the system. The computing system may include processing logic 802, such as microprocessors, controllers, field programmable gate arrays (FPGA), application specific integrated circuits (ASICs) electronic circuitry, and other types of logic. The processing logic 800 performs the operations of the computing device 802. A storage device 804 may also be provided. The computer readable medium and/or data storage device 804 may take various forms, including magnetic storage, optical storage, etc. Storage capability 804 may include computer-readable media, including removable computer readable media, such as disks, thumb drives and the like, or disk drives, solid state memory, random access memory (RAM), read only memory (ROM) and other types of storage. The computing device may include a display 806, such as an LCD display, an LED display, or other types of display devices on which video information may be displayed. The computing device 800 may include a network adapter 808 for interfacing with networks and a modem 810 for communicating wirelessly, over telephone lines or cable lines with remote devices. The processing logic 802 may use information stored in the storage device 804. In particular, the processing logic 802 may execute programs 814 stored in the storage and may access and store data 216 relative to the storage device 804. The computational functionality of the system described herein may be realized by the processing logic 802 executing the programs 814.

Figure 9:
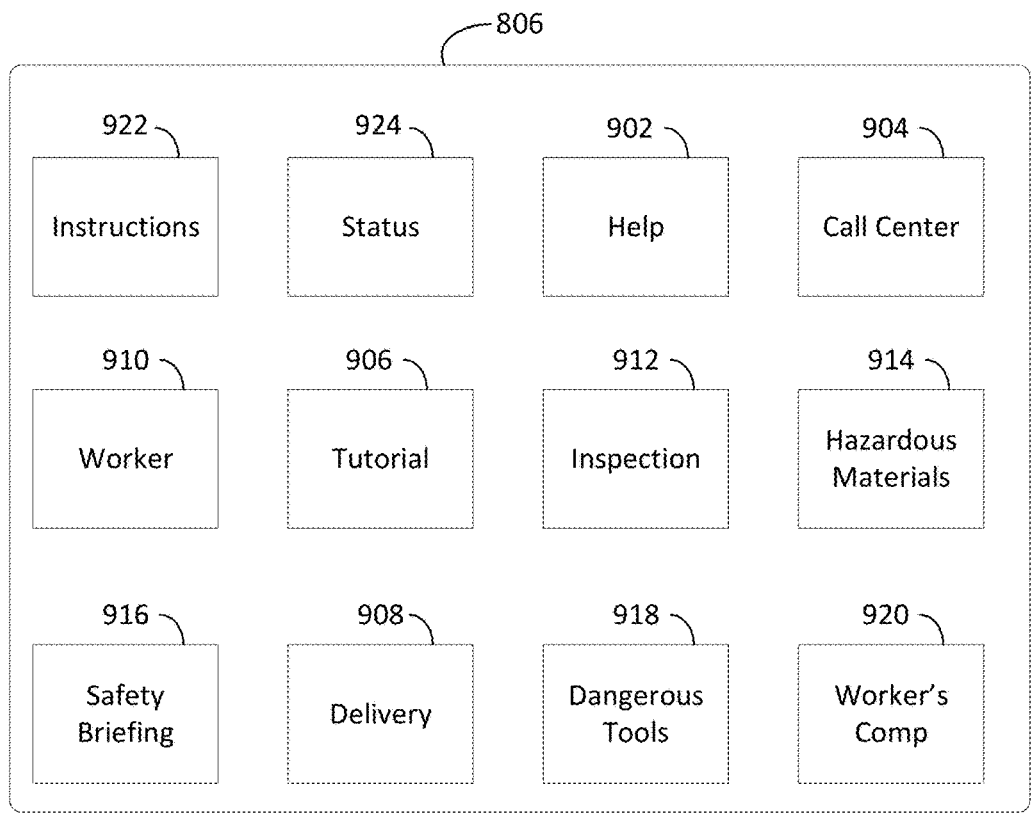
FIG. 9 is a schematic of aspects of the invention.

FIG. 9 shows an example of a user interface on display 806, such as found in the housing 400 In Figure. The user interface may include activatable elements. A user may depress these activatable elements or select these activatable elements using an input device, such as a mouse, keyboard, touchscreen, or the like, to activate the components. The display 806 may include a help element 902 that may be activated to obtain help information regarding use of the housing. It may also contain real time project or process plans. It may also include "how to" assistance including videos related to the various projects, stages, processes, and tasks performed at the project location. The user interface on the display 806 may also include a call center activatable element 904. Selection of the call center activatable element 904 may cause a call to be initiated with a call center so that the individual using the system may have a telephone and or video conference with personnel at the call center. The user interface on display 806 may also include a tutorial activatable element 906. Selection of the tutorial activatable element 906 causes a tutorial to be displayed to teach the individual about operation of the housing.

The system may include software which allows each tool to be coded or assigned to authorized personnel. Each tool can have a verifiably paired virtual representation associating the specific tool with the virtual representation. This can be verified by the system through recognition of the tool from a reader or sensor. The tool supplier record can be created by the tool supplier and include a virtual representation associated with the tool and store the virtual representation paired with the tool on the immutable storage. When the tool arrives at the project locations, the system can retrieve the tool supplier record and determine of the tool requested if the actual tool that arrived. A tool verification record can be created and stored on the immutable storage representing that the tool delivered and received matches the tool supplier record.

Shipping or delivery company personnel may activate the delivery activatable element 908 (FIG. 9). This causes a delivery functionality to be displayed where delivery notes may be added and where information may be gathered from the delivery person regarding a particular delivery.

An inspector activatable element 912, may be activated to cause the inspector functionality to be activated. The inspector functionality may enable an inspector to add inspection notes, provide electronic inspection certificates and the like. The system can provide reports that can be automatically generated from the existing data described herein as well as notes manually added during the construction process. The reports can be generated at predetermined times such as daily or upon completion of specific tasks.

Figure 10:
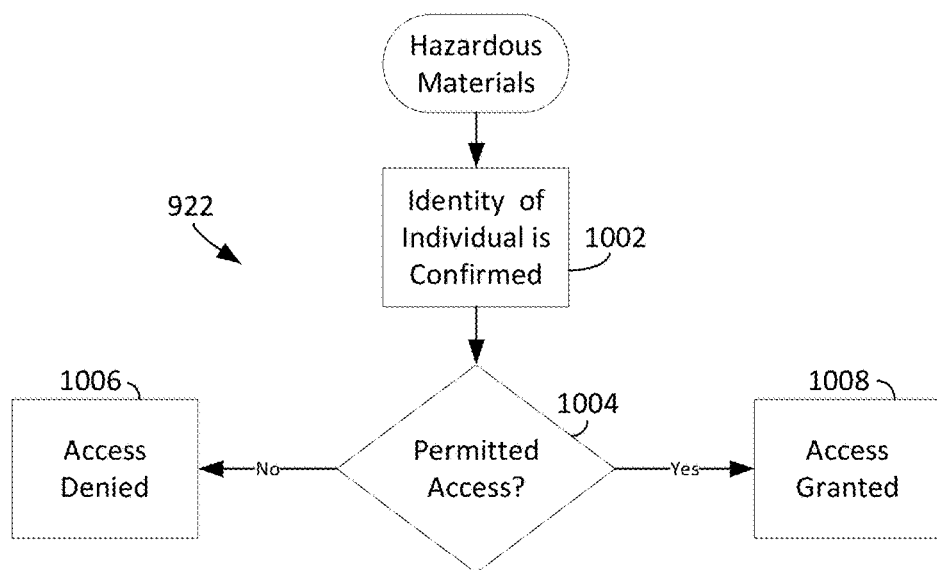
FIG. 10 is a flowchart of aspects of the invention.

Referring to FIG. 10, the system 1000 can include a process for allowing access to hazardous material. The identity of the individual can be configured at 1002. If the individual is permitted access at 1004, access is granted at 1008. Otherwise, access is denied at 1006.

Figure 11:
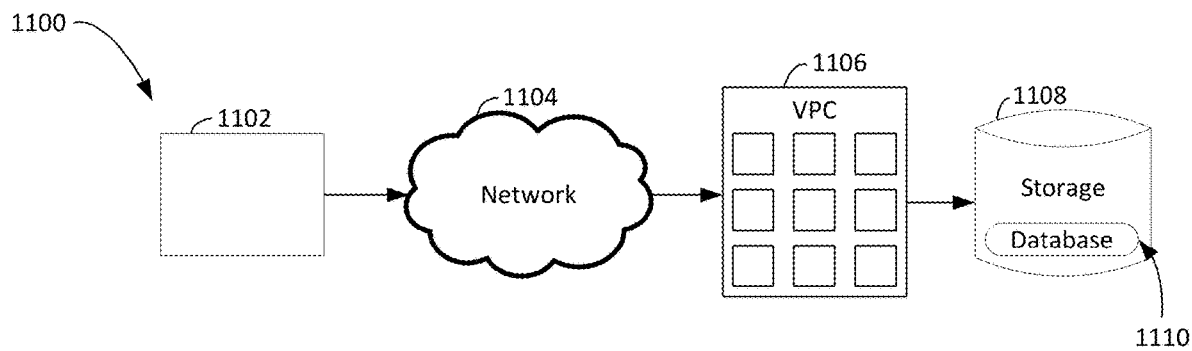
FIG. 11 is a schematic of aspects of the invention.

As shown in FIG. 11, the exemplary embodiments may be implemented in a decentralized computing environment 1100, that may include distributed systems and cloud computing. FIG. 11 shows one or more systems 1102 that may be in communication with a remote cluster 1106 via a network 1104. The cluster 1106 may store information received from the system 1102 and provide added computational functionality. The network may be a wired network or a wireless network or a combination thereof. The network 1104 may be a secure internet connection extending between the system 1102 and the cluster 1106, such as a virtual private cloud (VPC). The server may be a computing device and can be in communications with the site computer device. The cluster 1106 may include access to storage 1108. The storage 1108 may include a database 1110 in which information regarding a project location is stored in a consistent manner.

Figure 12:
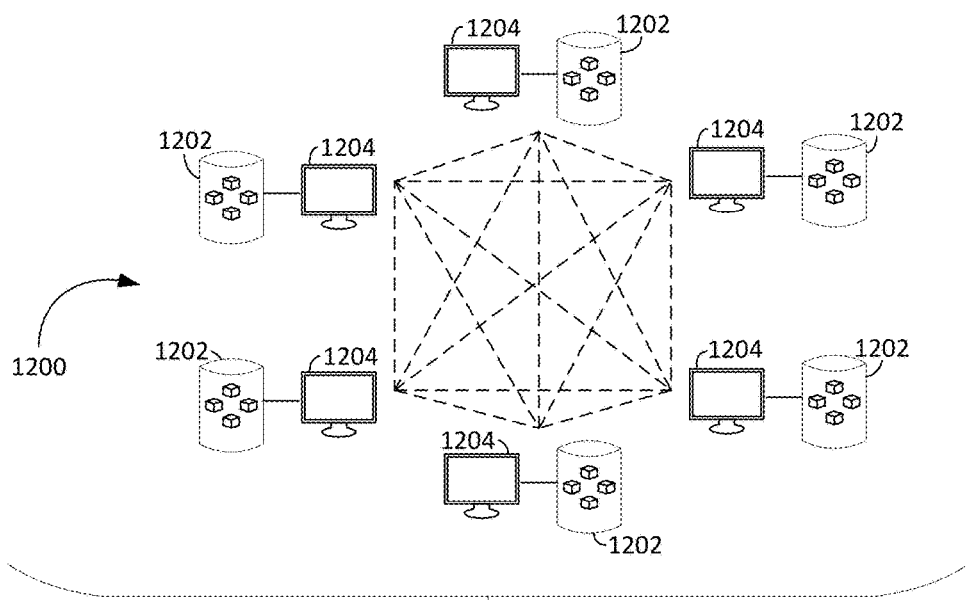
FIG. 12 is a schematic of aspects of the invention.

FIG. 12 shows diagram 1200 of an example of a peer-based network where an immutable storage 1202 is broadcast and shared among the nodes 1204. This network may be resident in the VPC cluster 1106 (FIG. 11) or in the network 1104 for example. The nodes 1204 may represent computing resources, such as server computer systems or other computing systems, residents at the parties identified in FIG. 12, for example. Each node that has access to a copy of the immutable storage 1202.

Figure 13A:
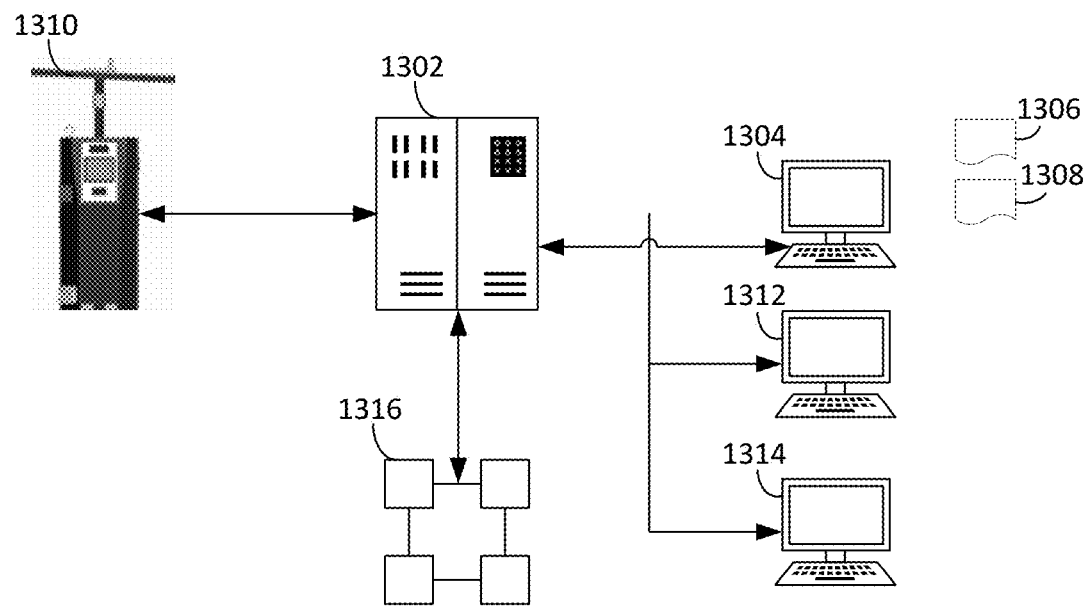
FIG. 13A is a schematic of aspects of the invention.
Figure 13B:
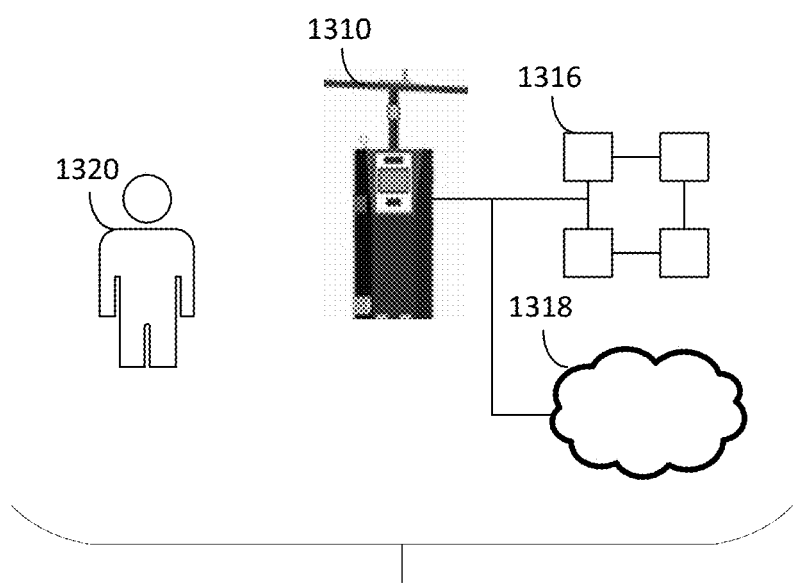
FIG. 13B is a schematic of aspects of the invention.

Referring to FIG. 13A, the various computer devices, including the server 1302 and site computer device 1310 (e.g., system, controller, and any combination), can be in communications with immutable storage 1316. The immutable storage can include a distributed ledger, immutable database, blockchain structure, and the like. The communications between the various computer device, including the server and the site computer device and immutable storage can be a global communications network, wide area network, or local area network, delivered to a computer readable medium from one device to another (e.g., USB drive, CD, DVD) and can be wired or wireless. Remote computer devices 1304, 1312 and 1314 can be in communications with the server 1302 and immutable storage 1316. Data 1306 and 1308 can be transmitted between the remote computer devices, the server and the site computer device. Referring to FIG. 13B, the site compute device 1310 is show in communications with the immutable storage 1316 and a global communications network 1318. The user 1320 can access the site compute device and therefore have access to data transmitted to and from the immutable server and remote computer devices via the global communications network.

Figure 14:
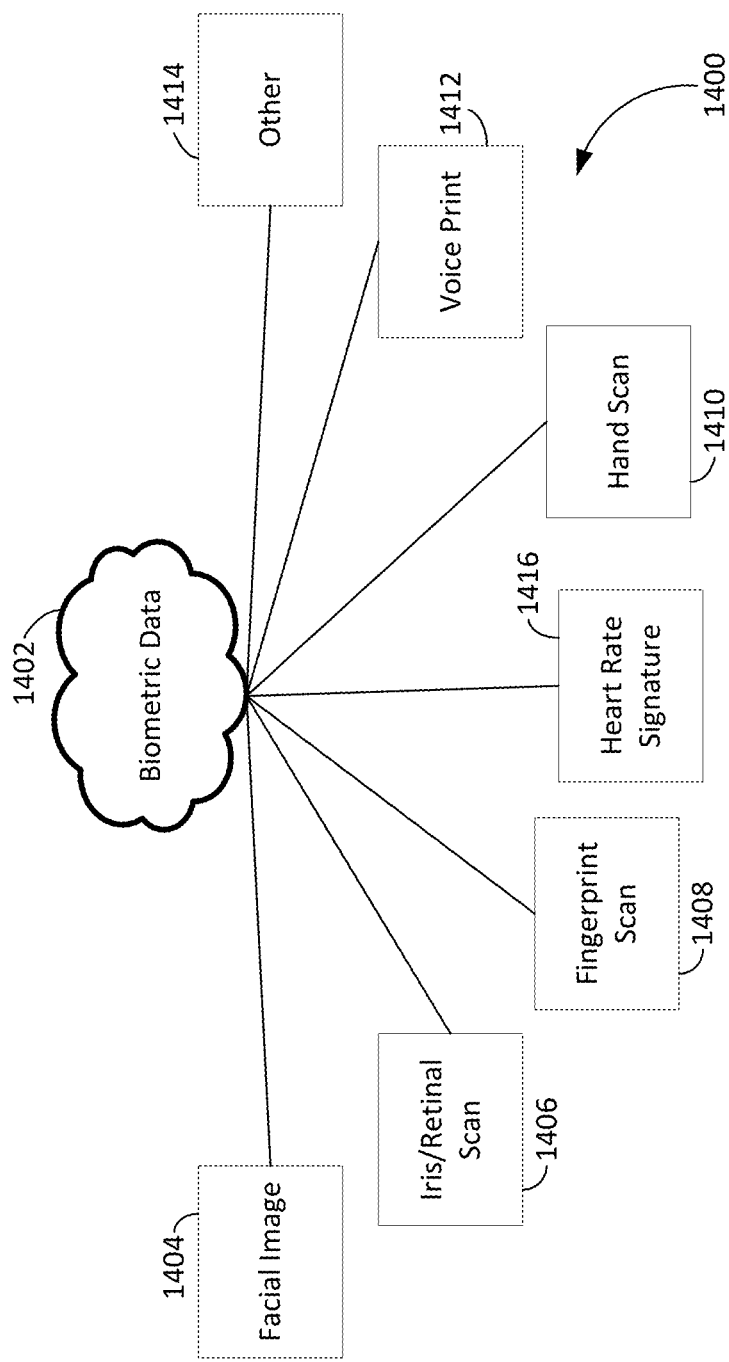
FIG. 14 is a schematic of aspects of the invention.

FIG. 14 shows a diagram 1400 that illustrates various types of biometric data 1402 that may be obtained by biometric-based identification devices at the project location to attempt to identify individuals. Biometric data may include facial recognition 1404, an iris/retinal scan 1406, a fingerprint scan 1410, a hand scan 1410, a voice print 1412 or heart rate signature 1416. It should be noted that other types 1414 of biometric data may also be used in exemplary embodiments to help identify individuals uniquely. Also, an individual may be required to provide multiple types of biometric data in some instances.

Figure 15A:
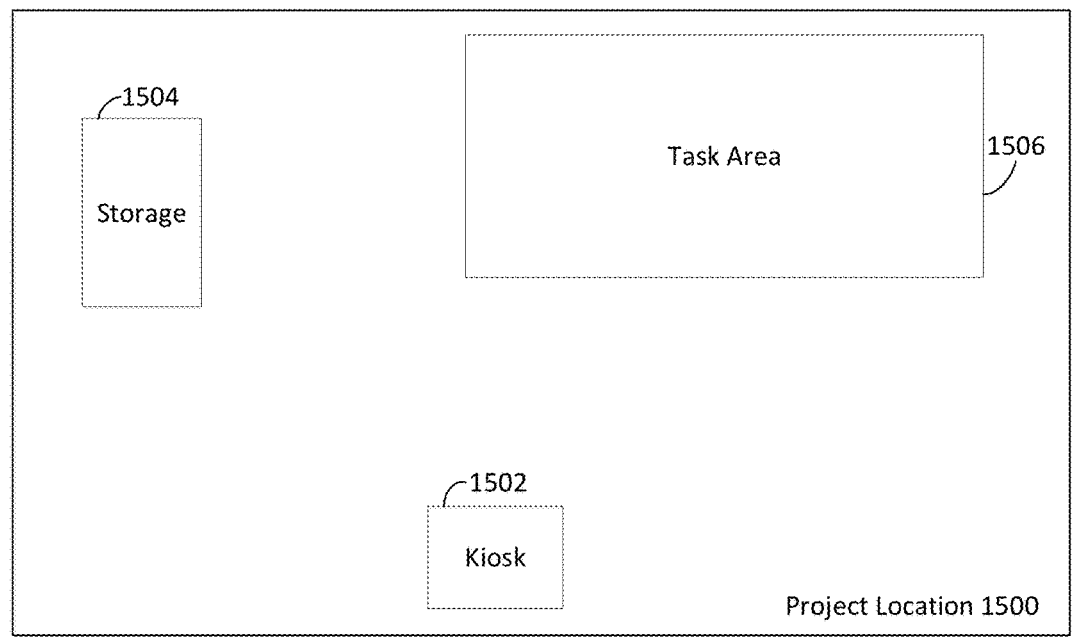
FIG. 15A is a schematic of aspects of the invention.

To help illustrate an example of geofencing, FIG. 15A shows an illustrative project location 1500. The project location 1500 may include a housing (kiosk) 1502 for the system as well as storage location 1504 that can be a building, trailer, shed or the like. The storage location 1504 may hold tools, equipment, wearables and/or materials. The project location 1500 may also include a task location 1506. The task location may be where tasks are performed using materials to produce a good or offer a service.

Figure 15B:
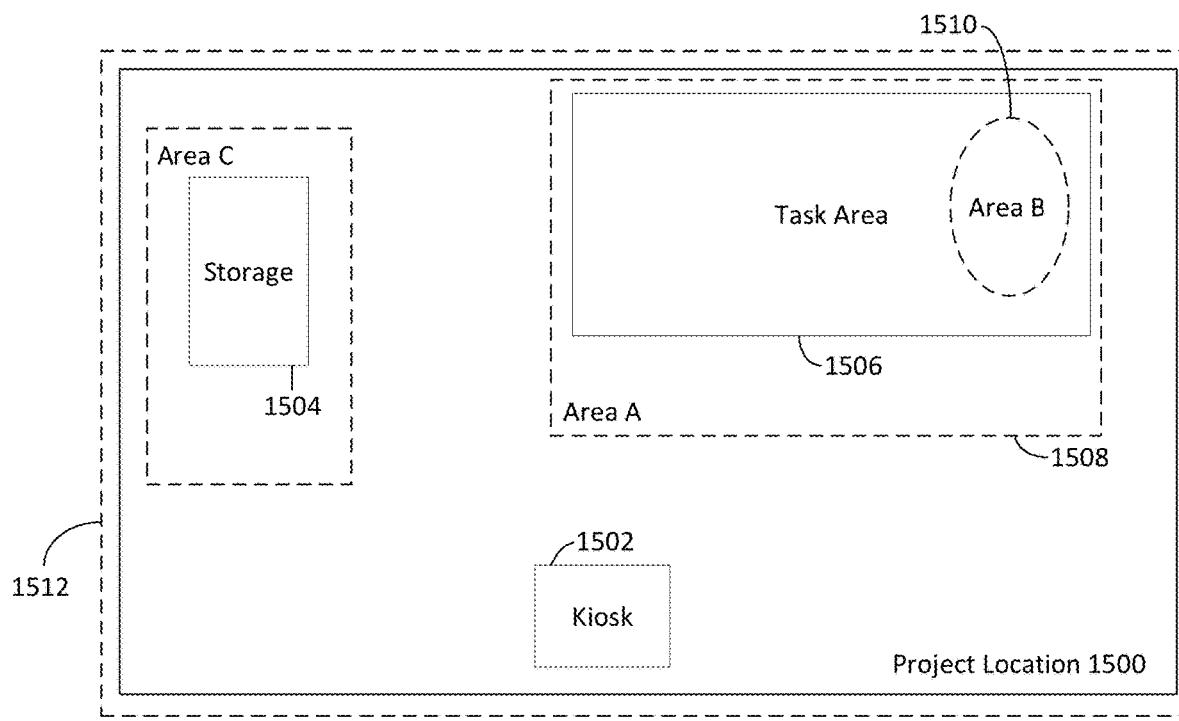
FIG. 15B is a schematic of aspects of the invention.

FIG. 15B shows an example of different areas that may be established for geofencing at the project location 1500. Area A shown a boundary 1508 may include the entirety of the project that is under construction 1506. Area B 1510 may be a portion of the project, such as the kitchen. Another area may be a shed and another area may be the entire project location. Individuals may have access to none of these areas or to a subset of these areas, including all areas.

Figure 16:
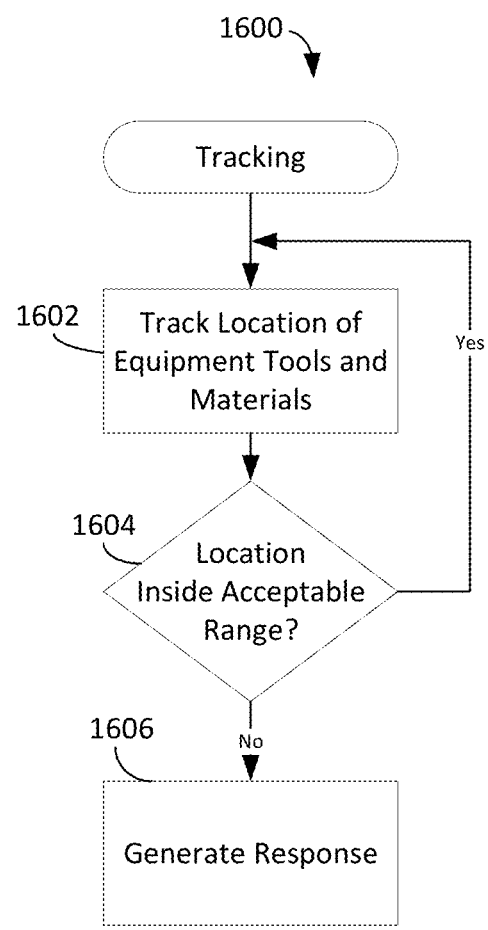
FIG. 16 is a flowchart of aspects of the invention.

Referring to FIG. 16, the system may track the location of equipment, tools, or materials at the project location 1602. The system can check whether the location of the equipment, tools or materials is acceptable or not 1604. For example, suppose that lumber has been delivered to the project location and the location of the lumber indicates that the lumber is removed from the project location. This would be problematic and would warrant a response. If the location is not acceptable as checked in 1604, a response is generated in 1606.

Figures 17, 18:
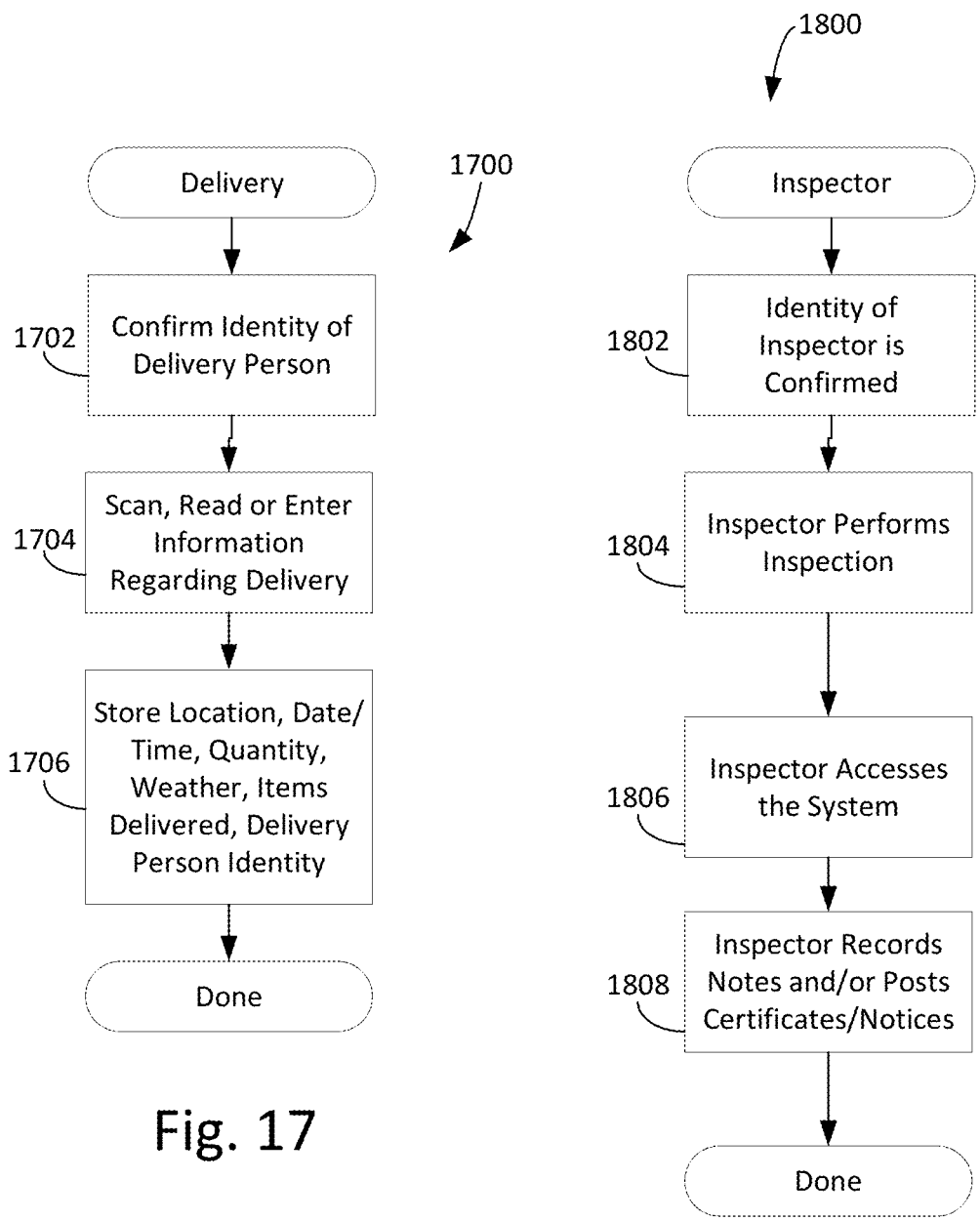
FIG. 17 is a flowchart of aspects of the invention.
FIG. 18 is a flowchart of aspects of the invention.

The system helps manage deliveries to the site. FIG. 17 depicts a flowchart 1700 showing steps that may be performed in this regard regarding deliveries. Initially, the identity of the delivery person is confirmed to indicate that the delivery person is the appropriate party and is permitted access to the project location 1702. For example, a serial number or other identification indicator may be scanned or read off the delivered items. In addition, information may be entered by the delivery person using the housing, such as by entering information via screen 408 (FIG. 4A) 1704. The location of delivery, the date of delivery, the time of the delivery, the quantity of the delivery, the identity of the delivery person and the weather may be recorded as part of the information that is kept regarding the delivery. This information can be used to track and confirm deliveries as well as to understand the conditions when the delivery was made.

The inspector may interface with the system. FIG. 18 includes a flowchart 1800 illustrating steps that may be performed in such an interaction. Initially, the identity of the inspector may be confirmed using the biometric data 1802 or manually using the touchscreen on the system. The inspector then performs the inspection of the appropriate portion of the project location 1804. The inspector then accesses the system, such as through the system at 1806. The inspector then may record notes and/or post certificates or notices at the system 1808. Additionally, the inspector may use technology available via the system such as OCR scanner or the like to capture appropriate information the inspector may have written during fulfillment of the reason for being on the site.

Inspection management information may be stored in the assembler database. Hashes of scheduled dates of inspections, dates of actual inspections and results and failed inspection reports for a project may be stored in the assembler database. The hash values may be passed to the management company database and referenced on the immutable storage.

Systems at adjacent locations may be used in conjunction with each other. For example, in the event that there are multiple smart indicia on one or more physical objects, the proximity of the indicium to each other can be used to verify the status, disposition and location of the one or more physical objects. In one indicium moves a certain distance from another, it can indicate a change in status that can be associated with an event record and the physical object.

Figure 19:
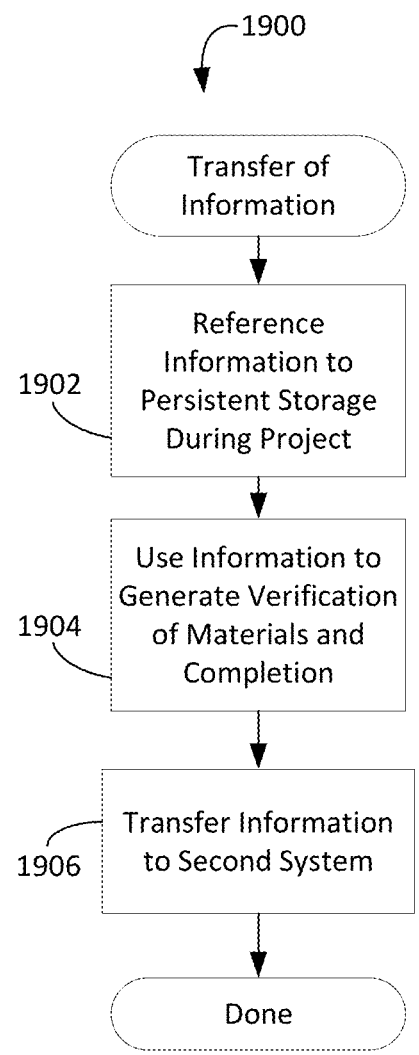
FIG. 19 is a flowchart of aspects of the invention.

FIG. 19 shows a flowchart 1900 of steps that may be performed when image capture devices, such as still cameras or video cameras, from multiple adjacently situated systems are used in conjunction in one example application. Video feeds or still images may be obtained from the image capture devices from multiple systems 1902. The video feeds or images may then be processed, such as by the cluster described above, using software such as motion detection software, thermal image analysis or other image analysis software to identify activity that may warrant a response 1904. When a motion is detected, it can trigger data capture for that event. The data can be transferred to a second computer or information system at 1906.

Figure 20A:
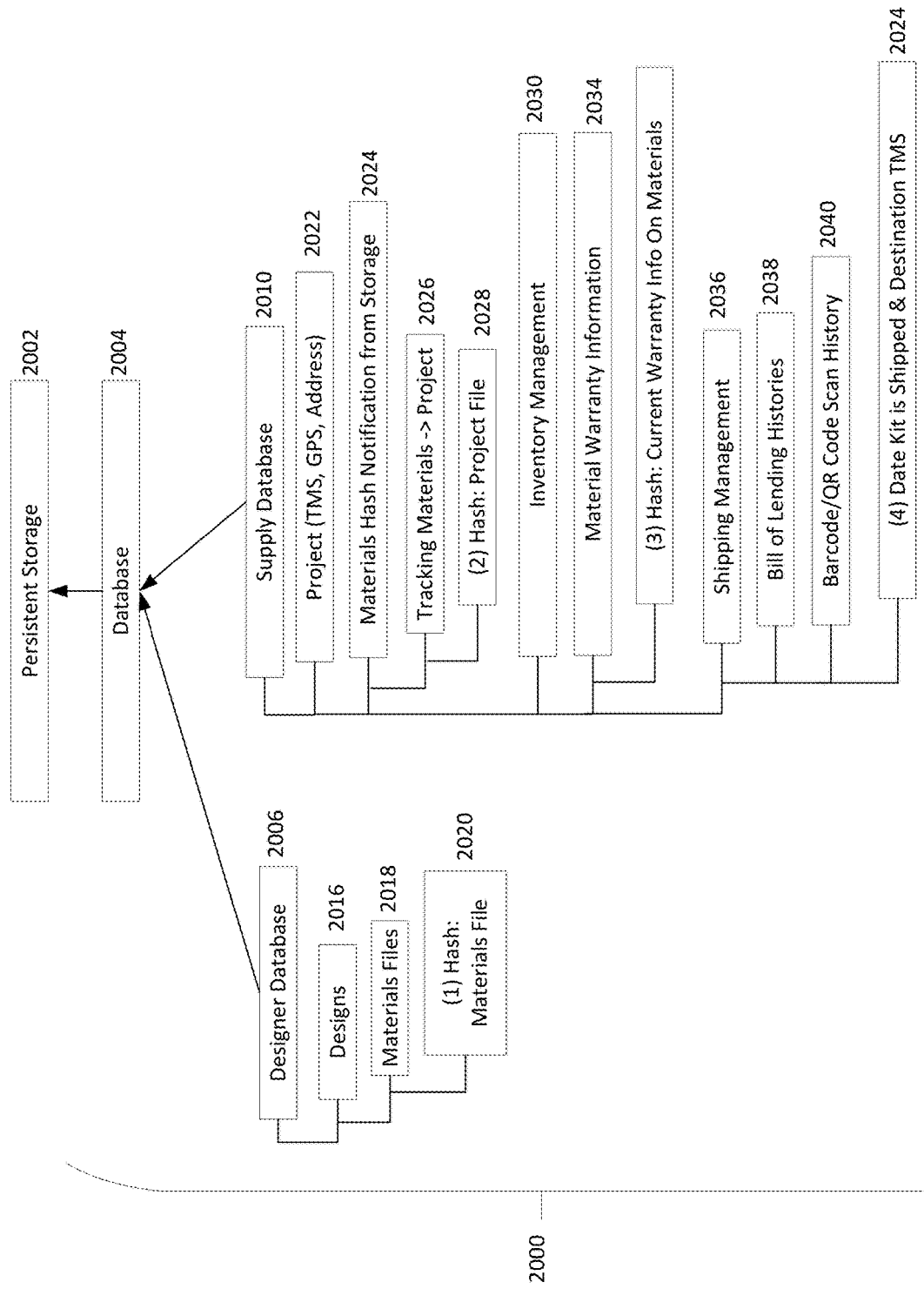
FIG. 20A is a flowchart of aspects of the invention.

As has been mentioned above, a great deal of information may be collected and stored during the project, process of task for reference during or after the project, process or task is completed. FIG. 20A shows a flowchart of steps 2000 that may be performed in exemplary embodiments in relation to the information. The information obtained during the project from many different sources may be stored on or referenced from immutable storage 2002. The information may be stored on an ongoing fashion, in databases as described below, and may be referenced in an immutable persistent fashion on the storage. This information may help resolve disputes between parties involved on the project or process. For example, suppose the assembler asserts that the wrong items were delivered. Since there is a complete record references on the immutable storage of all deliveries, these records may be accessed to resolve the dispute. Insurance providers may access injury records referenced on the immutable storage to settle or confirm claims. Disputes regarding pay among workers may be resolved by checking the recorded hours on site to determine the appropriate pay for the workers. Inspection records may be accessed to confirm that proper inspections were carried out and passed.

The information referenced in the immutable storage may also be accessed from a computing device of an owner, end user, customer, integrator, designer, and the like at 2006. The computing device may be, for example, part of a home maintenance system that manages and controls home systems, such as heating, air conditioning, lighting, an alarm system, or the like. The computing device may be part of a smart home controller and may interface with appliances and other items that are interconnected via a home control network. The computing device may include a document management system for securely storing the transferred information. The computing device may be a facilities management system, or operations system associated with the project location.

Figure 20B:
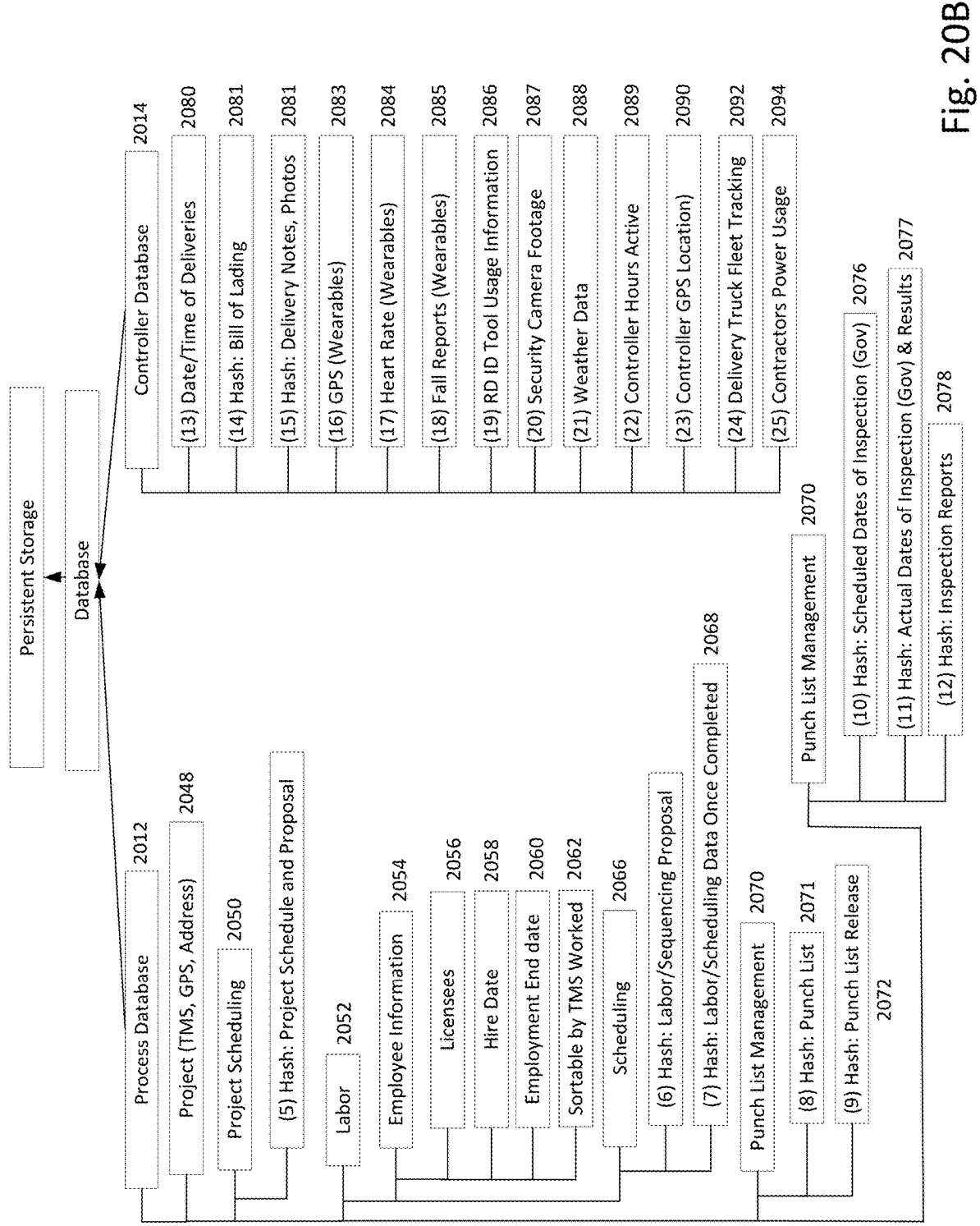
FIG. 20B is a flowchart of aspects of the invention.

FIGS. 20A and 20B show at 2000 depicting possible information from multiple data sources (e.g., databases), some of which may be referenced on the immutable storage 2002. The workflow may be that the data is first stored in a management company database 2004 and then referenced on the immutable storage 2002. The design company database may hold information that is passed on to the management company database 2004 and ultimately referenced on the immutable storage 2002. The design company database may hold designs 2016. The designs 2016 may include design and material files as has been discussed above. A hash value resulting from passing the material requirement record file 2020 for the project or process through a secure hash algorithm may also be stored on the design company database. The material requirement record file may be hashed using any number of different types of known secure hash algorithms as mentioned above. The hash value of the material requirement record file may be transferred to the management company database 2004 and then for reference on the immutable storage 2002.

FIGS. 20A and 20B also show a supply company database 2010. The supply company database 2010 may hold project information 2022, such as tax map submap (TMS) numbers, GPS data and addresses for project or process properties. The supply company database 2010 may store a material requirement record hash notification 2024 from the immutable storage 2002, indicating that the hash value for the material requirement record has been referenced on the immutable storage 2002. Information 2026 tracking the material requirement record may be stored in the supply company database. As was discussed above, the supply company may analyze and process the design to develop the material requirement record for the project or process. A hash value 2028 resulting from passing the design file through a secure hash function is stored in the supply company database 2010, transferred to the management company database 2004 and referenced on the immutable storage 2002.

The supply company database 2010 may also store inventory management information 2030, such as quantity and the particulars of material inventory and material warranty information for such materials 2032. The warranty information for materials used in the project may be hashed 2034 and the resulting hash value may be stored in storage in the supply company database 2010. The hashed value 2034 may be passed to the management company database 2004 and then referenced on the immutable storage 2002. The supply company database 2010 may also store shipping management information 2036. This may include bill of lading histories 2038 and barcode, RFID values, UHF values and/or QR code scan histories 2040. The material list (such as a bills of lading) for an assembly project and the barcode/QR scan codes for delivered items for the projects may be hashed 2042 and the resulting hash value(s) passed to the management company database 2004 for reference on the immutable storage 2002. Further, confirmation of what was specified by designers was delivered to the project location and installed according to the manufacturer's specifications so that a project or process can be placed under warranty.

An assembler database may store project information 2046, such as TMS #'s, GPS data and addresses for projects. The assembler database may also hold scheduling information 2048 for the project. This may include detail regarding workflow and timing. A hash value of the project schedule 2050 may be stored on the assembler database, passed to the management company database 2004 and referenced on the immutable storage 2002. The assembler database may store worker information 2052. The worker information 2052 may include employee information 2054 for workers involved in projects. This employee information 2054 may include information regarding licenses for workers 2056, hire dates for workers 2058, employment end dates for workers 2060 and other information, such as names, photos, etc. The worker or laborer information can include information that the worker or laborer is in compliance with applicable laws (including federal and state), in compliance with contractual obligations, properly licensed, of legal status, of sufficient experience, within application restrictions such as a limit on hours worked during a 24-hour period, authorized for the project location and any combination. The worker or laborer information may be sortable by keys such as TMS # to identify workers for a project. The assembler database 2012 may also store scheduling information 2064 for workers. This information may be used to develop a worker/sequencing proposal that is hashed 2066 and the resulting hash value stored in the assembler database 2012. The hash value 2066 may be passed to the management company database 2004 and referenced on the immutable storage 2002. Worker sequencing data once the labor is completed 2068 may be hashed and the resulting hash value stored in the assembler database 2012 for a project. This hash value 2068 may be passed to the management company database 2004 and referenced on the immutable storage 2002.

Punch list management information 2070 may also be stored in the assembler database 2012. The punch list management information 2070 may include a hash of the punch list for a project 2071 and a hash of punch list releases for a project 2072. These hash values 2071 and 2072 may be passed to the management company database 2004 and referenced on the immutable storage 2002. The punch list information can be used for a determination of warranty requirement compliance.

Figures 21, 22:
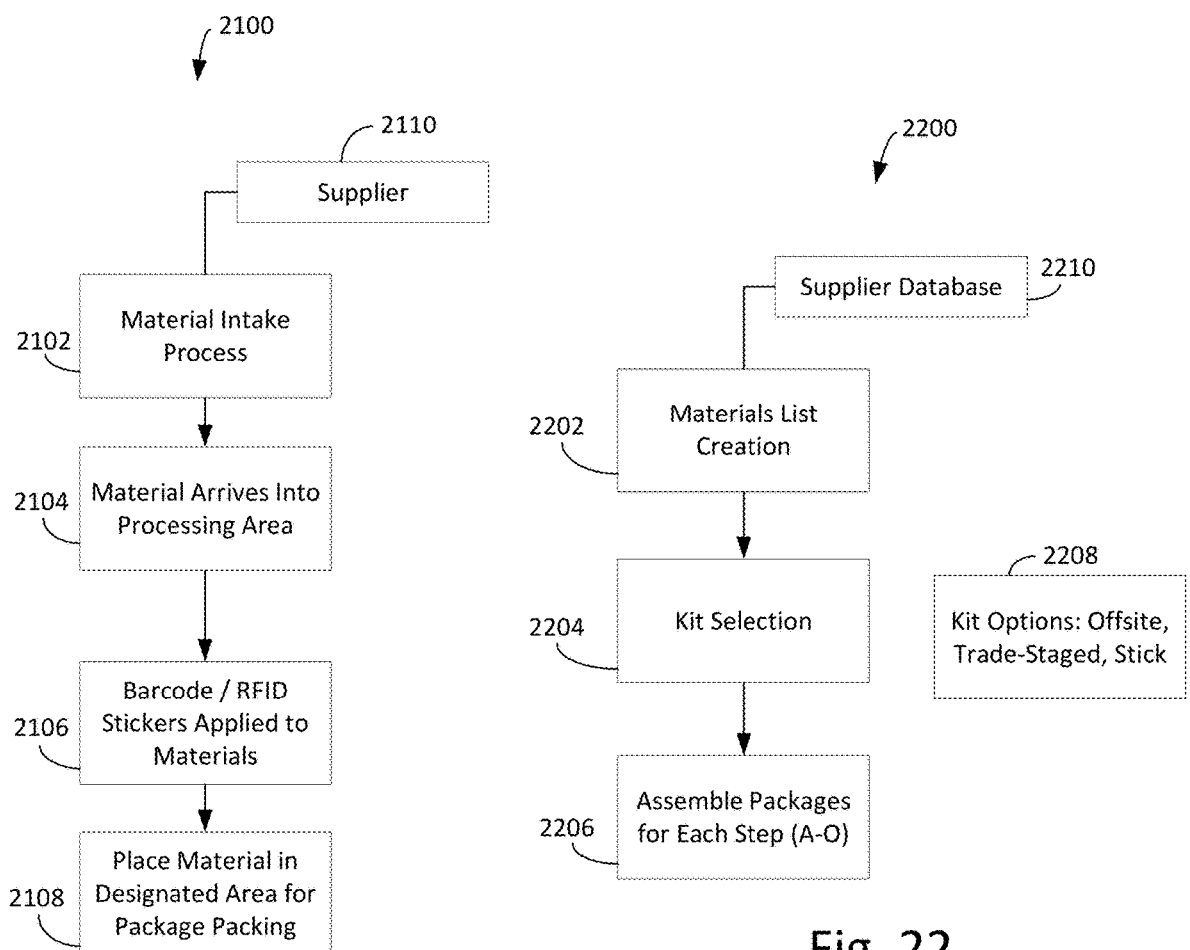
FIG. 21 is a flowchart of aspects of the invention.
FIG. 22 is a flowchart of aspects of the invention.

Referring to FIG. 21, the supply company 2110 is responsible for the intake of materials specified in the material requirement record that are needed for the project or process. Steps shown at 2100 are a material intake process 2102. Materials arrive 2104 at a processing area of the supply company 2110 from the manufacturers and/or distributors. Items such as barcode stickers, QR code stickers, Bluetooth beacons, UHF stickers and/or RFID stickers are applied to the materials 2106 so that the materials may be identified and tracked. The materials with the stickers applied are placed in a designated area for packing 2108. The materials may then be packaged for shipment to the project location.

As shown in the diagram of FIG. 22, the materials may be organized into kits for activities at the project location. The material requirements record 2204 is created at 2202 and processed to develop the set or group of materials that will be sent to the project location. Different strategies 2208 may be deployed to develop the set of materials. For example, the materials in the set may be staged based on the trade involved (e.g., electrical, plumbing, carpentry) so that each trade has its own set for the stage of construction. Thus, sets are selected 2204, and packages are developed for each step or stage of the project or process 2206.

Figure 23:
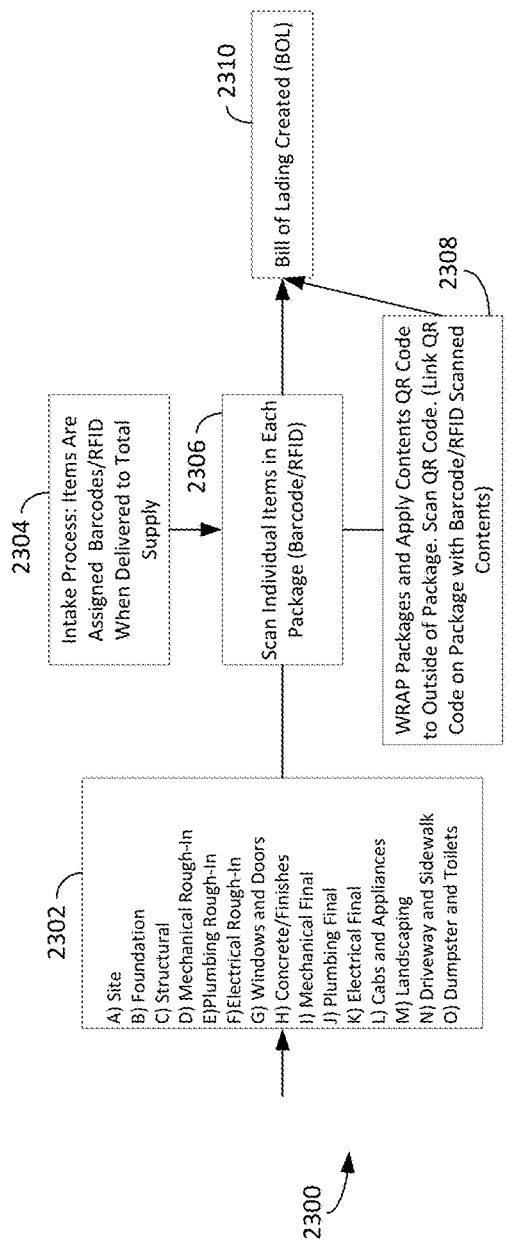
FIG. 23 is a flowchart of aspects of the invention.

FIG. 23 shows a diagram 2300 depicting additional detail of activity performed by the supply company. The project or process schedule 2302 is organized into stages, such as site preparation, foundation, etc. as shown. Items may be affixed, such as barcodes, QR codes, RFID identification, Bluetooth beacons and/or UHF identification when the items arrive at the supply company 2304. As was mentioned above, stickers may be affixed to the items to associate the codes with the items. The items in each package may be scanned to record what items are included in the packages 2306. The packages may be wrapped as needed and a QR code sticker may be affixed to the outside of each package 2308. The QR code for each package is scanned and the may then generate a material list for each delivery at 2310.

Figure 24:
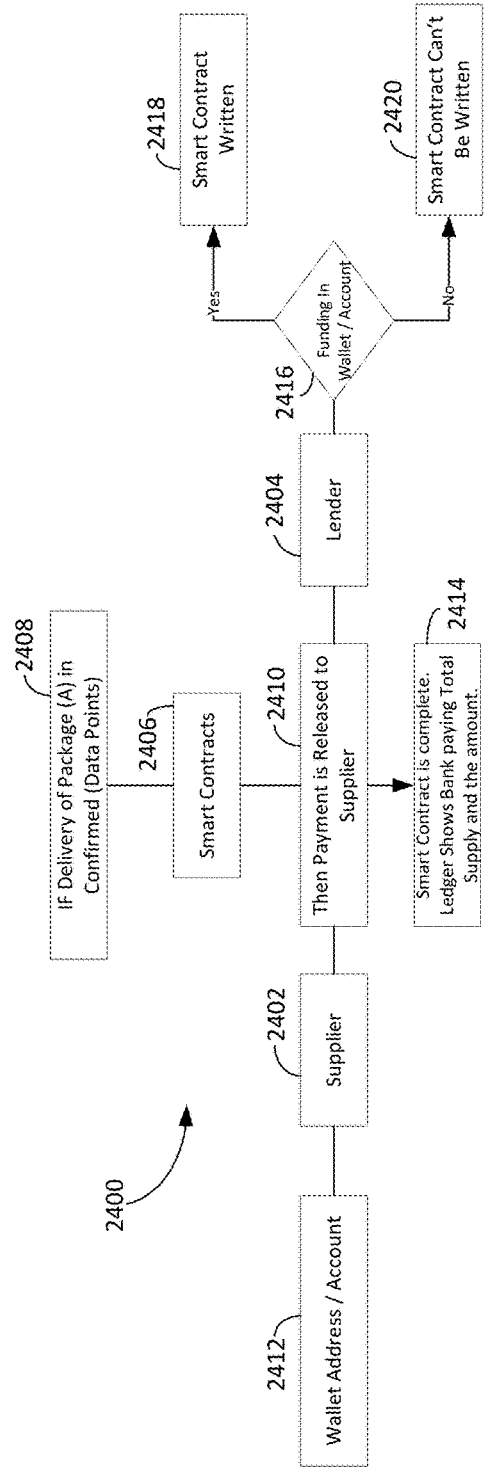
FIG. 24 is a flowchart of aspects of the invention.

FIG. 24 shows a diagram 2400 of a first example of interactions relating to a smart contract for the project or process. Suppose that the supply company 2402 makes a delivery to the project location. Further suppose that the delivery is confirmed 2408 by information such as that gathered by the system as discussed above. The lender 2404 then releases payment 2410 to the supply company 2402. Payments can be made through third party funding, factoring, credit lines, loans, or other financial option to assist with financing and cash flow management.

The payment may be made electronically, such as through crypto currencies, like Bitcoin or Ether, or via a stable coin whose value is pinned to an item like a paper currency or the like. A cryptocurrency is a digital currency built with cryptographic protocols that make transactions secure and difficult to forge. Other Suitable forms of electronic payment includes Automated Clearing House (ACH) payment, Electronic Funds Transfer (EFT), card payments, other types of bank transfers or other types of electronic wallet transfer. In the case where crypto-currency is used, the crypto-currency may be delivered to the digital wallet of the supply company at a specified wallet address or account 2412. The ledger may be updated to show that the contract is complete 2414. Payment requires that the lender has sufficient funding in their digital wallet 2416. If not, the smart contract will not be written on the immutable storage 2420. If there is sufficient funding, payment is made, and the contract is written onto the persistence storage as complete at 2418.

Figure 25:
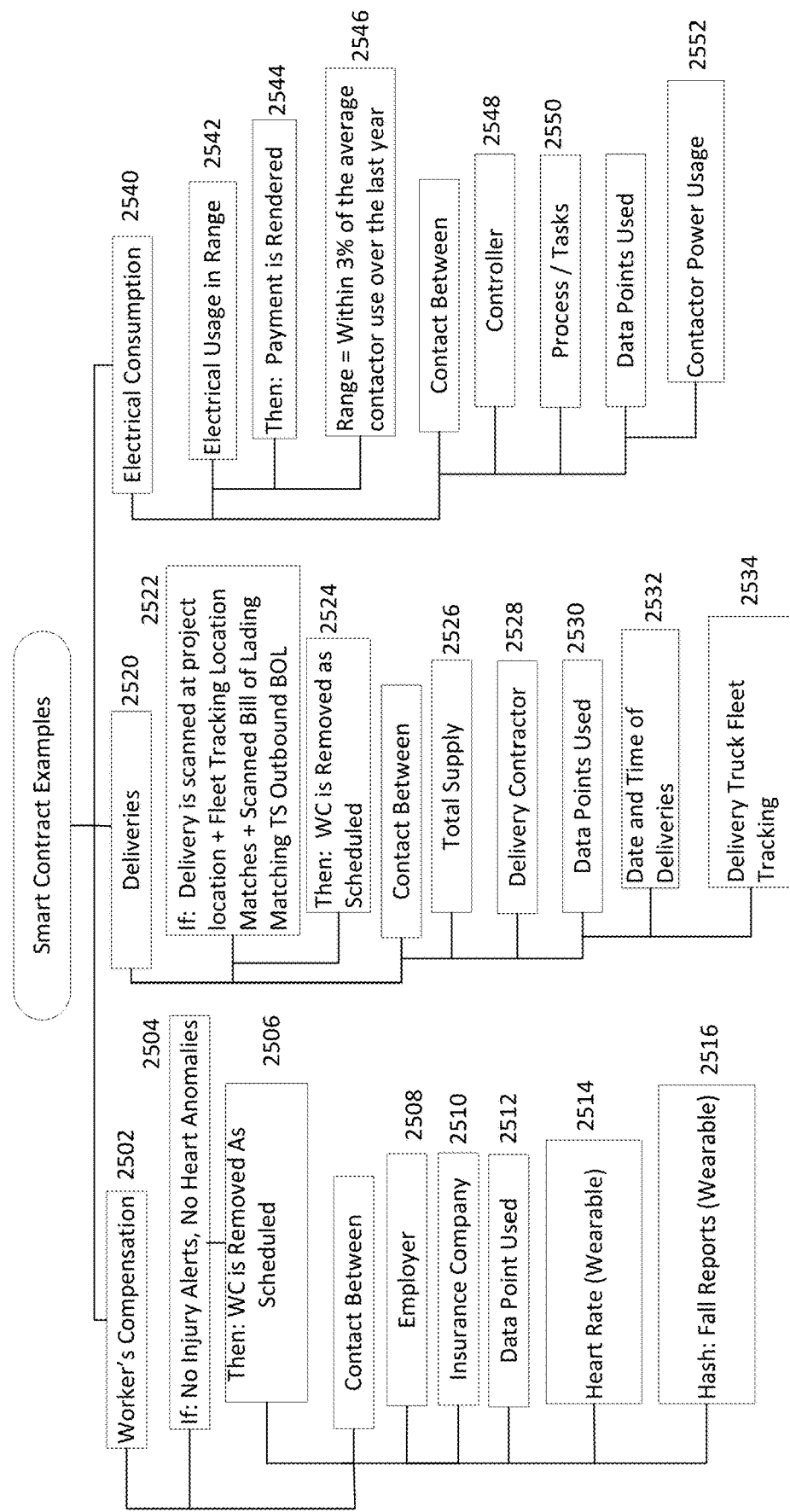
FIG. 25 is a flowchart of aspects of the invention.

FIG. 25 depicts a diagram for multiple illustrative smart contracts. In a first illustrative smart contract, the smart contract concerns worker's compensation insurance 2502. The contract removes the insurance for a worker 2506 if there are no injury alerts and no heart rate abnormalities for a given worker 2504. The smart contract can be between entities such as employers (e.g., an assembler) 2508 and an insurance company 2510. The contract looks at the data points 2512 of the heart rate history 2514 gathered by a wearable for the worker and any fall reports 2516 from a wearable for the worker. As mentioned above, the wearables may include a gyroscope or other mechanism that provides data indicative of a fall. This data may be processed to identify data indicative or a fall or other incident where an injury may have occurred.

A second illustrative smart contract shown in FIG. 25 relates to payment for a delivery 2520. If a scan is made at the delivery site, if the fleet location tracking information matches the desired delivery site location and if the scanned material list at the delivery site matches the outbound material list from the supply company 2522, then payment from the supply company 2526 to the delivery worker 2528 is made. Data 2530 used by this illustrative smart contract 2530 includes date and time of deliveries 2532 and delivery truck fleet tracking information 2525.

A third illustrative smart contract shown in FIG. 25 relates to electrical consumption 2540. If the electrical usage by a worker of the assembler is within a range of 3% of the average worker use over the past year 2542 and 2546, then payment is provided 2544 by the assembler 2550 to the system 2548. Power usage data 2552 can be reviewed.

There can be a relationship between the smart contracts and the project schedule. Initially, the project schedule is received. As discussed above, the assembler forms the project schedule based in part on the design and material requirement record. Based on the project schedule, smart contracts may be constructed that use the immutable storage for contractual arrangements associated with the project or process. The smart contracts are implemented in software and in this case are used to provide electronic payments to parties for activities relating to the project or process using, for example, electronic payments, crypto currencies, fiat currencies and other forms of payments. The smart contracts may specify the conditions required for payment and may specify the amounts of payment.

Figure 26:
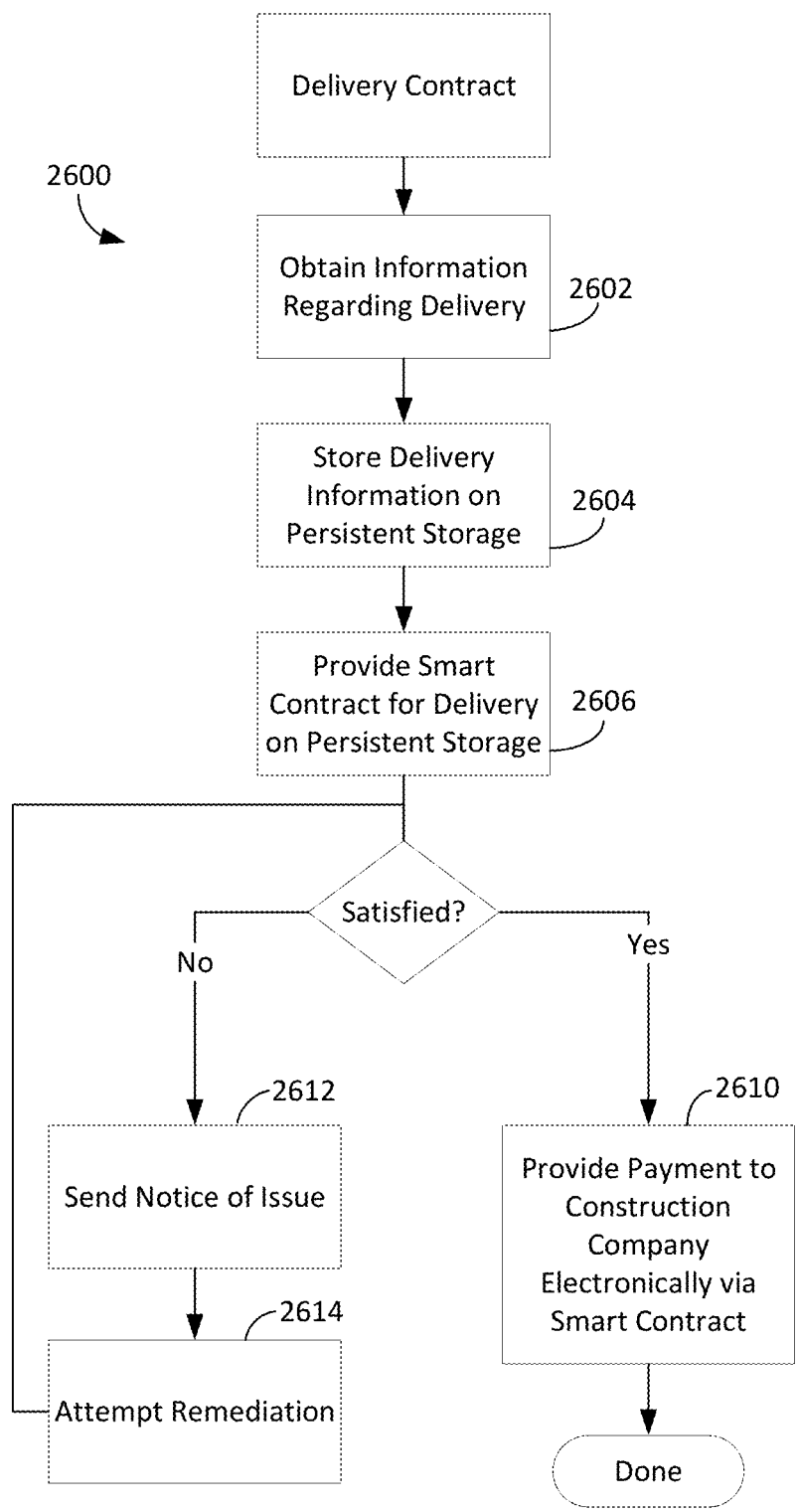
FIG. 26 is a flowchart of aspects of the invention.

Smart contracts may also play a role with deliveries. FIG. 26 provides a flowchart 2600 concerning steps performed in relation to deliveries relating to such smart contracts. First, delivery and/or materials information is obtained regarding delivery to the project location for the project or process 2602. The information obtained can include if the materials delivered match the material requirement record, manufacturer, and/or supplier which can be confirmed by multiple parties.

The delivery information is hashed, and the resulting hash value is referenced on the blockchain-based immutable storage 2604. A smart contract is provided that uses the immutable storage 2606. A determination is made whether the conditions specified in the smart contract are satisfied 2608. If the conditions are satisfied, electronic payment for the delivery is realized 2610. If the conditions are not satisfied, notice of outstanding issues are sent and the delivery worker may attempt to remedy the issues 2614. The process may then repeat beginning with step 2608 until the conditions are satisfied.

To pair a material with its virtual representation the system captures events at various points of transition of the material. Pairing the physical material with the virtual representation can include several elements or components. Included in the pairing process can be the physical observation of the physical material and then associate the physical material with a virtual representation so that the physical material is properly associated with the virtual representation. This verification provides trust that the virtual representation is accurately associated with the physical material as a factor rather than simply trusting that the virtual representation is accurate. This system can use manual or automated processes to physically observe the material and associate the material with the virtual representation during various events from raw material to final deliverables. Verification can also use the metadata that is associated with the interaction of physical items by individuals and electronics when the item is created, transported, installed, activated, and destroyed. The metadata that can be captured and placed into immutable storage can provide stakeholders an audit trail of history for their physical asset using a verified paired virtual representation. A similar process as described herein can be used for pairing a biometric identifier with an individual.

For example, when raw material is harvested, a harvesting record can be created that captures the harvesting event and can include metadata concerning the event and verification that the raw material is associated with the harvesting record. For example, a digital image of the raw material can be captured, and the images and its metadata of the image captured can be included in the virtual representation. The capture device and its metadata can also be captured and included in the harvesting record. For example, a sensor having a GPS transponder, camera and transceiver can be used to capture the harvesting event. The metadata of the harvesting event can include date, time, location (e.g., GPS coordinates), harvesting image, harvesting entity, harvesting worker, harvesting equipment and any combination. Once harvested, raw material can be loaded on a transport (e.g., vehicle, plane, ship, and the like). By capturing the harvesting event and verifying that the raw material and the virtual representation are paired, and stored on the immutable storage, the physical material and the virtual representation are paired allowing for reliance upon the digital record to accurately represent the physical material.

In one embodiment, the verification of the physical object can be performed using the weight or dimensions of the physical object captured throughout a process. The weight and dimensions can be combined with one or more images of the physical object where the capture device can be a scale, scanner, or other device. The capture device can be a combination of a camera and scale to provide for data streams during the process and at and between events.

By verifiably pairing the physical asset with a virtual presentation, the risk of unintentional or impermissible rehypothecation can be reduced or eliminated. The paired asset can be verified by multiparty chronological metadata streams that can be associated with a physical location. Because verifications using these streams are chronological, altering the information could require alteration of the metadata prior to and after the altered record. Therefore, the altered record would be inconsistent with the associated records potentially both temporally and geographically and an attempt to alter the record would be discovered. The use of an immutable storage further reduces the risk of alterations of records as well as increasing the verification of information. Further, pairing assets associated with the event, involving the asset, interactions with the asset and the associated metadata provide for a substantiated digital asset, reduce, or eliminate risk and improve capital efficiency. Further, the pairing of assets facilitates commerce by allowing electronic transactions with assurances that the virtual representation used in the electronic transaction is paired with the physical asset.

Verification, including verification of an event, can include verifying that the physical material and the virtual representation match and can be accomplished in a variation of methods including interaction with identification elements such as a tag, label, and the like, capturing an image of the material, capturing a video of the material, capturing indicia such as a tag physically affixed or otherwise associated with the material, human visual inspection, weight measurements at and between events, capturing the dimensions of the physical object at and between events, and any combination. Identification of an individual performing or otherwise associated with an event can be captured by identification devices (e.g., cards, tags, RF ID. smart dust, beacons) and biometrics including visual capture (e.g., facial recognition), voice recognition, iris scan, fingerprint, palm print and any combination.

The system can retrieve the harvesting record, receive verification that the raw material delivered to a shipper is the same that was harvested and create a shipping record. A verification that the physical material and the retrieved virtual representation match can be performed using a capture device, worker verification and a combination. The metadata associated with delivering the raw material to the shipper can be captured and included in the shipping record. The shipping record can include information about the shipper and the worker delivering the raw material to the shipper. The shipping record can include information about the destination of the raw material. By capturing the shipping event and verifying that the raw material harvest delivered to the shipper and the virtual representation are paired, and stored on the immutable storage, the physical material and the virtual representation are paired from harvesting the delivery to the shipper allowing for reliance upon the digital record to accurately represent the physical material and its disposition.

The system can retrieve the shipping record, receive verification that the raw material delivered by the shipper to a processor (e.g., manufacturer), is the same that was harvested, shipped, and received. The metadata associated with delivering the raw material to the processor can be captured and included in a delivery record. The delivery record can include information about the shipper, processor, worker and any combination. The delivery record can include information about the processor, location, and other information. By capturing the delivery event and verifying that the raw material harvest delivered to the processor and the virtual representation are paired, and stored on the immutable storage, the physical material and the virtual representation are paired from harvesting the delivery to the processor allowing for reliance upon the digital record to accurately represent the physical material and its disposition.

Once the processor processes the raw material to form a processes material, the system can create a processor record including that the raw material delivered to the processor is integrated into a processed material and is the same raw material that was harvested, shipped, and received. The metadata associated with processing the raw material can be captured and included in a processing record. The processing record can include information about the harvesting, shipping, processor, worker, and any combination. By capturing the processing event and verifying that the raw material harvested delivered to the processor and the virtual representation are paired, and stored on the immutable storage, the physical material and the virtual representation are paired from harvesting to processing allowing for reliance upon the digital record to accurately represent the physical material and its disposition.

Once processed, the processed material can be further shipped to be included as a component in another material. For example, the raw material can be aggregates, rocks, Portland cement and water. The processed material can be concrete. When an article (material) is made from the concrete, the article can be associated with a virtual representation that allows pairing of the article with the raw material and the events through the article process. Therefore, the physical article and the virtual representation are paired from harvesting to article creation allowing for reliance upon the digital record to accurately represent the physical article (material) and its disposition.

Referring to FIGS. 27A through 27E, persistent storage 2700 shows different types of inputs 2702 that may be used for assisting gathering information regarding deliveries. A machine vision system 2704 may be provided. The machine vision system 2704 may capture an image of the delivered items and process the image to determine the nature of the items that were delivered as well as the quantity of items. Moreover, the machine vision system may capture an archival image that may be indicative of the state of the items when they were delivered. A QR code scanner may be used where QR codes are on a delivered items or documentation. Similarly, a bar code scanner may be used where bar codes are on the items or on documentation delivered with the items. Still further, an RFID reader 2710 may be provided to gather information regarding the delivered items.

a user of the supplier computer system can select or otherwise acquire an object such as material identified on the material list 2704 from a materials requirement record 2708 or designer record that can be retrieved or otherwise received by the supplier computer system from the immutable storage 2700. The supplier can verify that the material matches the material requirement record at 2710, and the system can capture this event such as by creating a material record 2714. For example, one method of associating the physical material with a virtual representation is using a indicia ($I_1$) 2720a placed on the material. The indicia can then be physically verified to be associated with the material from the material list or the material requirement record. Therefore, the physical material and the virtual representation ($V_1$) are paired by recording this event and associating the physical material, $I_1$, and $V_1$. In one embodiment, the indicia can include the following information:

| Description | Digits | Information |
|---|---|---|
| Locations | 19-20 | GPS XX.XXXXXX XXX.XXXXXX |
| User ID | 8 | SSN XXXX + Initials XX + Gender X |
| Date | 10 | XX/XX/XXXX |
| Time | 7 | Zulu XXXX:XX |
| Material | 12 | UPC/Barcode XXXXXXXXXXXX |

An event record 2718 such as a supplier record can be created and stored on the immutable storage. The capture event can include a unique number and include the supplier ID, date and time, location, material ID, status, and any combination. The material ID can be from an original manufacturer or the supplier. The status can include that the material has been gathered, packaged, ordered, is in stock or on back order, shipping information and any combination. The shipping information can include the origin, destination, shipping instructions, shipper, and any combination.

A shipper can retrieve shipping information 2722 from the immutable storage 2700 identifying the material location, load, destination, pick time, delivery time, and other information concerning the shipping of the materials. The shipper can verify that the physical materials being retrieved from the supplier match the virtual representation of the supplier record. If the materials are verified, the shipper can physically capture the event, for example, by affixing its indicia 2720b ($I_2$) to the materials representing this verification. A supplier shipping pickup record 2724 can be created and stored on the immutable storage. The supplier shipping pickup record can include project, shipper, material, status, date, time, location, and any combination. The mode of transportation of the material can also be tracked and stored on the immutable storage. For example, if the shipper uses a vehicle, the date, time, location, and other metadata associated with the vehicle can be gathered along the route and stored on the immutable storage. Verification can be provided using the metadata of the various events. For example, if the date, time, and location of the supplier record is within a certain range of values of the date, time and location of the supplier shipping pickup record, there will be verification that the proper materials were physically transmitted from the supplier to the shipper.

The shipper can deliver the material to the destination such as a project location. When the shipper delivers the materials to the project location, the shipper can capture this event by creating a supplier shipping delivery 2728 record using a shipper computer system 2730. The shipper can verify the event by methods including adding a indicia 2720c ($I_3$) representing that the proper materials were delivered to the proper location. The project location computer system 2732 can be used to verify that the materials were properly delivered by retrieving the material record 2714 from the immutable storage and using the record to match the physical materials delivered. In one embodiment, the shipper can use the tags that are part of the virtual representation to match 13 with the material and the information stored on the immutable storage to capture and verify the event. When the material is delivered, the project location can use a project computer system 2732 to retrieve the material record from the immutable storage and match the material delivered with the material record. The project location can add an indicia 2720d ($I_4$) to the material to capture this event. The project location can create a project location material received record 2734 that can include the project, material, virtual representation ($V_4$), status, date, time, location, other metadata, and any combination. The shipper, worker at the project location, or both can physically inspect the material and verify that it is matches the virtual representation stored on the immutable storage. This verification can be included in the information that is stored on the immutable storage by the shipper and a worker or system at the project location.

Figure 27A:
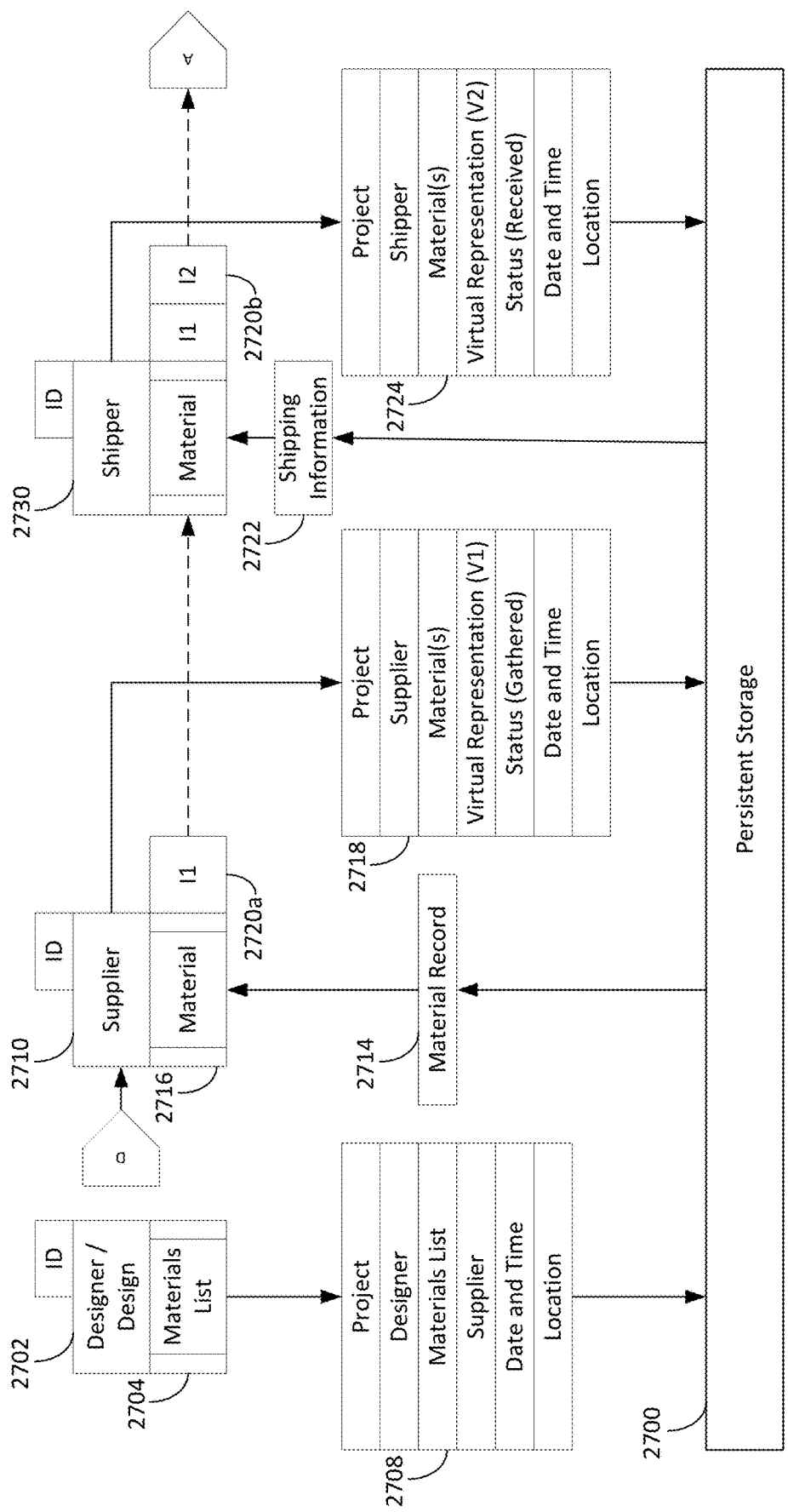
FIG. 27A is a flowchart of aspects of the invention.
Figure 27B:
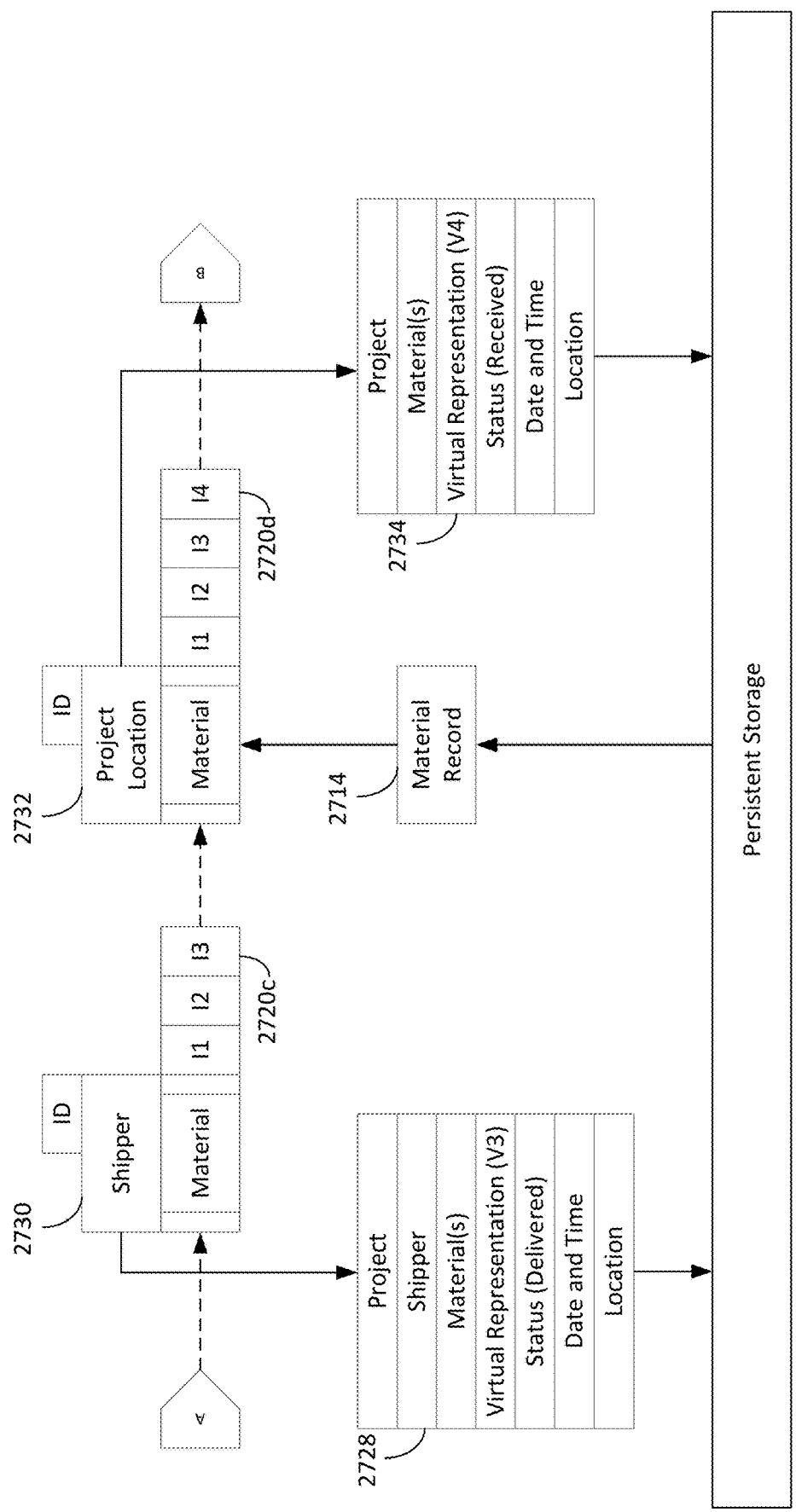
FIG. 27B is a flowchart of aspects of the invention.
Figure 27C:
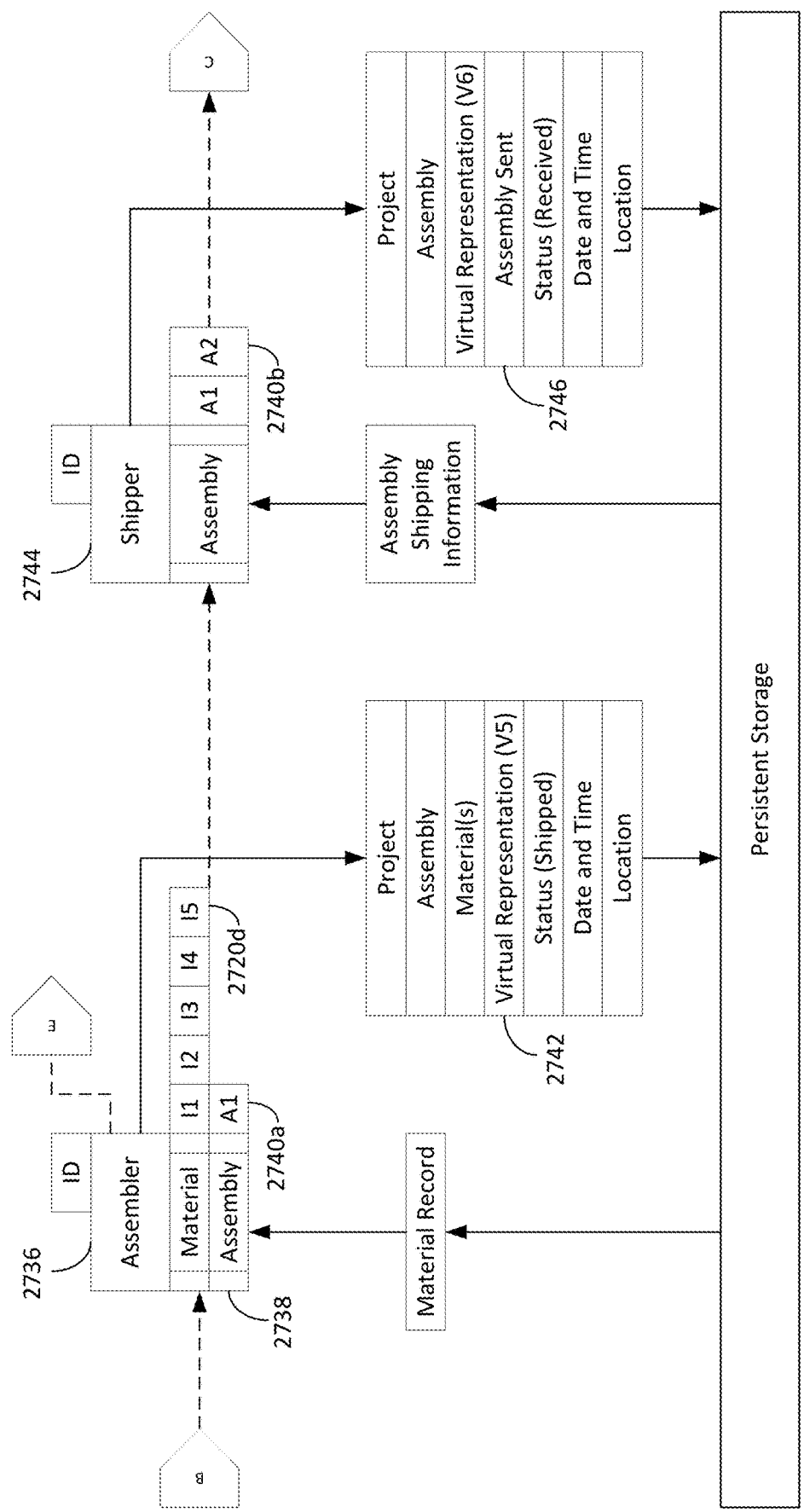
FIG. 27C is a flowchart of aspects of the invention.

Referring to FIG. 27C, the project location can be an assembler, or the assembler can be at a separate location from the project. For example, in the manufacturing of a vehicle, the project location can be the assembly line for the vehicle and multiple assembly locations can be involved. The main assembly line can be the project location and the assembler can be a component or sub-component of the manufacturing process. This system can be used for the project, or sub-project that are included in the overall project. Further a sub-project can be treated as a project as discussed herein.

An assembler computer system 2736 can be used to retrieve the material record from the immutable storage. The material record can be used to match the materials delivered to the assembler to verify that the proper materials were received by the assembler. The assembler can add indicia 2720d ($I_5$) to the material, or use other verification methods described herein, to capture the event. The assembler can also capture the material used and the assembly 2738 by adding a indicia 2740a ($A_1$) to the assembly. An assembler record 2742 can be created and stored on the immutable storage. The assembler record can include the project, assembly description and other information, assembler, material(s) used, virtual representation, shipping information date, time, location of the assembly, other metadata, and any combination.

One verification can be the comparison of an image of the physical object taken at the first event and the image of the physical object taken at the second event. In one embodiment, the determination if the two images represent the same physical object can be made by comparison the distance between the images. The distance between the images of the two object captures do not have to be identical but can be defined by the "closeness" between the images. In one embodiment, the distance can use the Euclidean distance between the $i^{th}$ and $j^{th}$ physical object. Distance between the p-dimensional vectors can be represented as:

$$d_E(i, j) = \sqrt{\left(\sum_{k=1}^{p} (x_{ik} - x_{jk})^2\right)} \quad (1)$$

or by using the weighted Euclidean distance that can be represented as:

$$d_E(i, j) = \sqrt{\left(\sum_{k=1}^{p} w_k(x_{ik} - x_{jk})^2\right)} \quad (2)$$

Where $d_E$=distance, i=first image, j=second image, and w=weight between kth measure which can be subject to the following $$0 < w_i < 1 \text{ and } \Sigma_{i=1}^{n} 1 \quad (3)$$

In one embodiment, the verification process can include an individual retrieving the first image of the physical object and comparing the first image with the physical object in proximity of the individual. The individual can review the first event record and the second event record to also make a determination of the physical object has remained the same from the first event to the second event. Information. In one embodiment, multiple individual and computer system can make the comparison. The comparison can also be crowd sourced so that multiple verifications are made from individual computer systems.

Once completed, the assembly may need to be delivered to another location. The assembler record can include shipping information, or an assembly shipping record can be created and stored on the persistent record. If the assembly needs to be delivered, a second shipper can use a second shipper computer system 2744 to retrieve the shipping record, assembler record or other shipping information that is used to identify the origin, locations, assembly, pick up time, delivery time and other information associated with the transportation of the assembly from one location to another. The assembly can be received by the second shipper and the second shipper can capture the event such as with a indicia 2740*b* ($A_2$) to the assembly representing that the assembly has been verified by the second shipper as properly provided and received by the shipper. A second shipper pick up record 2746 can be created and stored on the immutable storage.

Figure 27D:
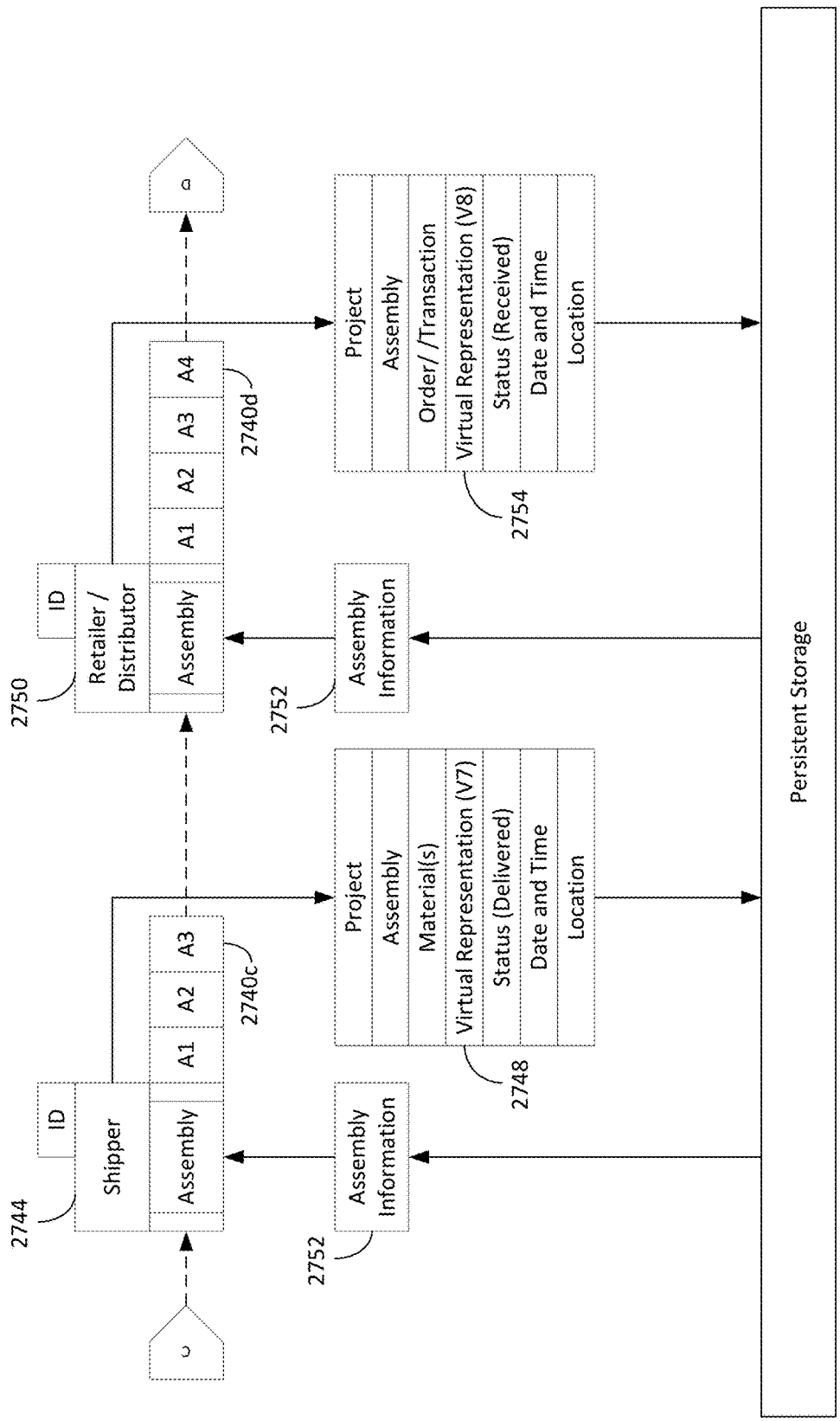
FIG. 27D is a flowchart of aspects of the invention; and,
FIG. 27E is a flowchart of aspects of the invention.

Referring to FIG. 27D, the second shipper can deliver the assembly to a retailer, distributor, or customer. The assembly can be a component to be further used or a final product. When the second shipper delivers the assembly to a retailer or distributor, the second shipper can create a second shipper delivery record 2748 using a second shipper computer system 2744. The second shipper can capture the event such as using a indicia 2740*c* ($A_3$) representing that the proper assembly was delivered to the proper location. The second shipper can use the verifications that are part of the virtual representation to match $A_3$ with the material and the information stored on the immutable storage.

The retailer or distributor computer system 2750 can be used to verify that the materials were properly delivered by retrieving the assembly record 2752 or second shipper record 2748 from the immutable storage and using the record to match the physical assembly delivered. The retailer or distributor can capture the event and can add a indicia 2740*d* ($A_4$) representing that the proper assembly was received at the proper location. A retailer distributor record 2754 can be created and stored on the immutable storage.

Figure 27E:
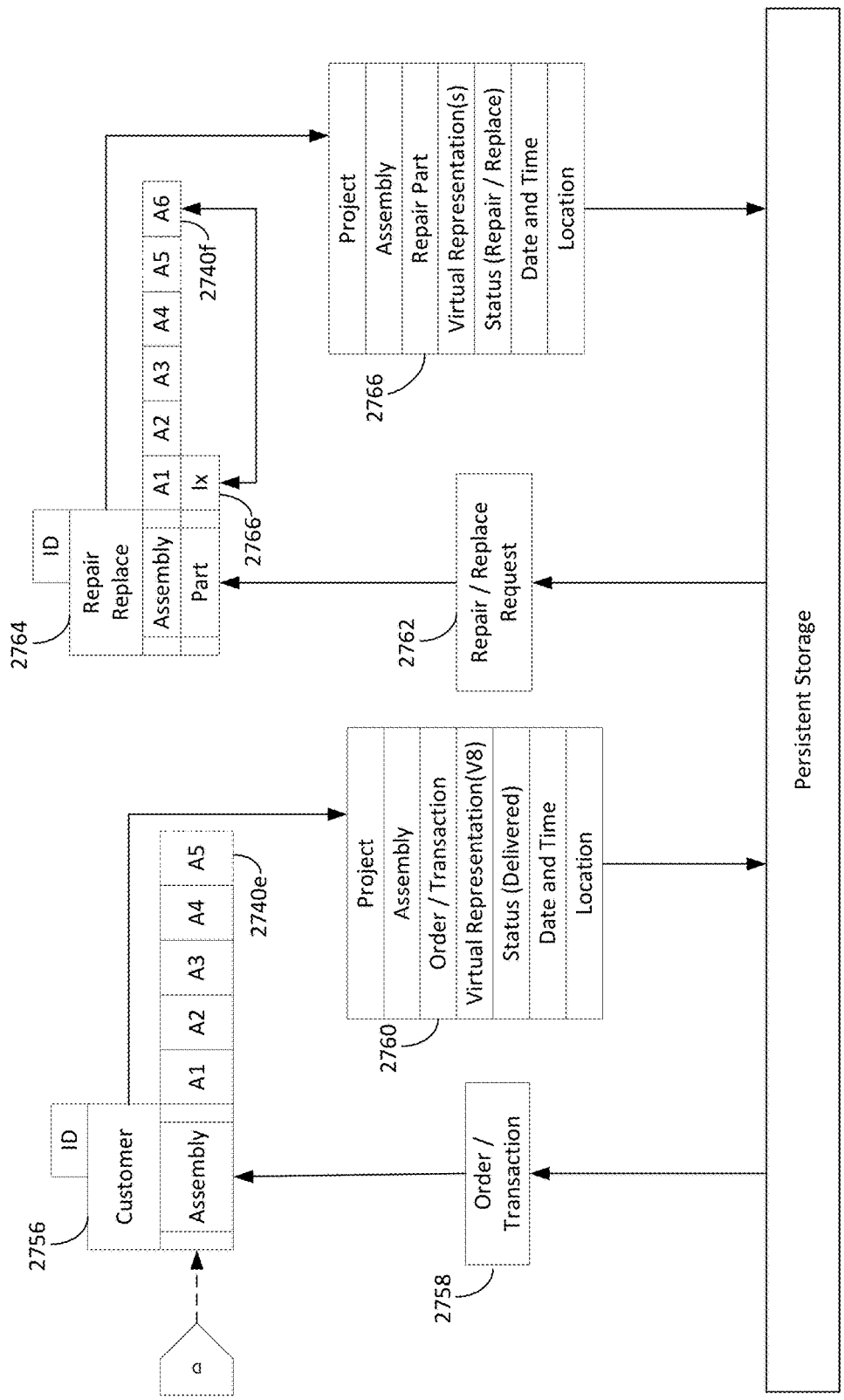

Referring to FIG. 27E, a customer can receive the assembly as using a customer computer system 2756 to retrieve or otherwise receive an order record 2758 from the immutable storage or other system requesting that a customer receive the assembly. The customer can be shipped the assembly using the system as described herein with a shipper performing the steps and the system performing the steps associated with the shipper and second shipper above. A third shipper can create a third shipper pickup and delivery record that can be stored on the immutable storage verifying that the assembly was properly provided from the realtor or distributer to the customer. The customer may capture the event and can add a indicia 2740*e* ($A_5$) to the assembly that can be associated with the virtual representation ($V_8$). A customer record 2760 can be stored on the immutable storage.

Using this system, the customer can be assured that the assembly was independently verified and authenticated from the design to the delivery to the customer and that the virtual representation of the assembly and its components (e.g., materials) are paired.

In one embodiment, a repair request 2762 can be created and stored on the persistent server. The repair request can be associated with the assembly and retrieved by a repair computer system 2764. The repair company can receive a part using the system described herein, perform a repair or replacement action, and capture the event such as by using a indicia 2740*f* ($A_6$) to the assembly indicating that the assembly has had a part repaired or replaced. The repair part can also have a preexisting indicium from the use of the system herein and the repair company can capture the event such as by using a indicia 2768 ($I_x$). A repair record 2766 can be created and stored on the immutable storage.

The system described herein can pair the physical material and/or assembly with a virtual representation. Failure to pair the physical material or assembly with the virtual representation can negatively impact areas such as regulatory requirements. Regulatory requirements are a set of rules that can specify the standards for a project. Regulatory requirements impact designs, materials, worker's license and experience the project and process. For example, a building code may require that construction materials be installed in accordance with manufacturer's specifications and warranty regulations. Failure to follow the building codes can result in the project not being approved, errors, lack of customer satisfaction, insurance claims, injury, litigation, and other negative ramifications. Tracking, management, and verification of materials to ensure compliance with regulatory requirements and proper installation according to applicable specifications is an important aspect to many projects and processes. Tracking and record keeping during the project or process can be beneficial, as it can be difficult to perform these tasks after project or process completion because the materials can be hidden from view or otherwise inaccessible. For example, electrical wiring in a project or process can be hidden behind walls and ceilings once the project is complete.

Systems at multiple locations may be interconnected using image capture devices, RFID, QR codes, barcodes, biometric scanners, still cameras, video cameras, and the like to identify individuals or machines that are performing verifications during the process. Further, multiple individuals or machines are performing verifications so that there is not a reliance upon any one entity for verifications. The processing of capturing data, including images, from the multiple systems at multiple locations can be used to improve the verification of proper materials and assemblies as well as to pair the physical items with the virtual representation.

Verification of processes, inspections, completions and deliveries with adjustments and notifications (manual and automated) with confirmation would ensure increased productivity, especially if accessible in real time at the location. Real time processes and procedures planned with corresponding training and manuals would improve quality control and efficiency. This has been a long felt need in the prior art that has not been satisfied with a controller that is uniquely associated with an asset location.

Automated verification of quantities, quality, and correct product deliveries along with after delivery tracking of materials with accountability is seldom used. Designated delivery areas with geofenced control and tracking of materials once delivered would help prevent loss. Confirmation of products integrated at the asset location provides transparency regarding sourcing, warranties, as well as future reference during the structure and individual product's life of use.

By using the various tags and virtual representations, each entity in the process can verify that the physical materials match any record the precedes that entity.

This process can include internal and external individuals and machines for performing inspections (e.g., verifications) . For example, the system can receive a set of internal inspection information entered into the system from an internal inspector representing an internal physical inspection of the project, material or assembly. As the items travel, an internal inspector can provide inspection information representing the stages of the project. The system can also receive a set of external inspection information from an external inspector and an external inspection computer device representing a third-party physical inspection of the project at predetermined stages of the project. Based upon the internal inspection, external inspection or both, an inspection record can be created and stored on the immutable storage.

The verified pairing described herein can also be used to verifiable pair physical assets with installation instructions, storage instructions, warranties, ownership, service, maintenance, and any combination thereof.

The system can also facilitate the use of digital wallets. The information that is contained on the digital wallet can be paired with a physical object so that transactions associated with the physical object can be conducted with verification that the digital representation in the digital wallet represents the physical object, whether the physical object is fungible or unique.

What is claimed is:

1. A computerized system for verifiably pairing a physical object with a digital representation comprising:
   a computer system in communication with an immutable storage;
   a first data capture device in communications with the computer system;
   a second data capture device in communications with the computer system;
   a set of computer readable instructions included in the computer system configured for:
      receiving a first event record from the first data capture device including a first location, a first time and a first set of metadata wherein the first set of metadata includes an original digital representation captured by the first data capture device of the physical object,
      receiving a subsequent event record from the second data capture device including a second location, a second time and a second set of metadata wherein the second set of metadata includes a subsequent digital representation captured by the second data capture device of the physical object, and,
      comparing the original digital representation to the subsequent digital representation, creating a verification representing that the object transitioned from an originating event to a subsequent event according to the original digital representation matching the subsequent digital representation.

2. The computerized system of claim 1 wherein the set of computer readable instructions include instructions for comparing the original digital representation with the subsequent digital representation, determining a difference between the original digital representation and with the subsequent digital representation and generating a notification when the difference is within a predetermine range.

3. The computerized system of claim 1 wherein the first data capture device is remote from the computer system.

4. The computerized system of claim 1 wherein the subsequent event record includes a verification data representing that verification of the physical object subject to the subsequent event is the same physical object associated with the originating event according to the first event record.

5. The computerized system of claim 4 wherein the set of computer readable instructions include storing the first event record on the immutable storage and the set of computer readable instructions are adapted for retrieving the first event record form the immutable storage, comparing the first digital representation with the subsequent digital representation includes retrieving the first event record from the immutable storage.

6. The computerized system of claim 4 wherein the subsequent event record includes a verification data representing that an individual viewed the metadata of the first event record and compared it with the physical object.

7. The computerized system of claim 1 wherein the second set of metadata is taken from sources from the group consisting of public records, enterprise software, a local computer device and remote computer device and any combination thereof.

8. A computerized system for verifiably pairing a physical object with a digital representation comprising:
   a computer system in communication with an immutable storage;
   a set of computer readable instructions included in the computer system configured for:
      retrieving a first event record from the immutable storage wherein the first event record includes first location, a first time and a first set of metadata wherein the first set of metadata includes a first digital representation captured by a first data capture device of the physical object,
      retrieving a subsequent event record from the immutable storage including a second location, a second time and a second set of metadata wherein the second set of metadata includes a subsequent digital representation captured by a second data capture device of the physical object, and,
      comparing the original digital representation with the subsequent digital representation to determine when a difference between the original digital representation and the subsequent digital representation is within a predetermine range.

9. The computerized system of claim 8 wherein the set of computer readable instructions include instructions for comparing the the first digital representation with the subsequent digital representation after the occurrence of a second event.

10. The computerized system of claim 8 wherein the subsequent event record includes a verification data representing that verification of the physical object subject to the subsequent event is the same physical object associated with the first event.

11. The computerized system of claim 10 wherein the subsequent event record includes a verification data representing that an individual viewed the metadata of the first event record and compared it with the physical object.

12. A computerized system for verifiably pairing a physical object with a digital representation comprising:
   a computer system in communication with an immutable storage;
   a data capture device in communications with the computer system;
   a set of computer readable instructions included in the computer system configured for:
      retrieving a first event record from the immutable storage wherein the first event record includes a first location, a first time and a first set of metadata wherein the first set of metadata includes a first digital representation captured by a first data capture device of the physical object,
      creating a subsequent event record from the data capture device including a second location, a second time and a second set of metadata wherein the second set of metadata includes a second digital representation captured by the data capture device of the physical object, and,
      comparing the first digital representation the second digital representation;
      determining a difference between the first digital representation and the second digital representation.

13. The computerized system of claim 12 wherein the set of computer readable instructions includes instruction for determining if the difference is within a predetermine range.

14. The computerized system of claim 12 wherein the instructions for determining a difference between the first digital representation and the second digital representation includes retrieving the first event record from the immutable storage.

15. The computerized system of claim 12 wherein the subsequent event record includes a verification data representing that verification of the physical object subject to the subsequent event is the same physical object associated with the first event according to the first event record.

16. The computerized system of claim 12 wherein the the data capture device is a first data capture device; and, wherein the computer readable instructions for determining a difference between the first digital representation and the second digital representation includes retrieving a first image of the physical object, comparing the first image to a second image captured by a second data capture device, and creating a verification when the first image matches the second image representing that the same physical object is present at the second time and the second location.

17. The computerized system of claim 12 wherein the instructions for determining a difference between the first digital representation and the second digital representation includes capturing an object indicium affixed to the physical object, comparing the indicium on the object at the subsequent event to a digital indicium included in the first event record.

18. The computerized system of claim 17 wherein the indicium is taken from the group consisting of a still image of the object, a label affixed to the object, a radio frequency identification tag, an ultra-high frequency tag, a bar code, a QR code, a Bluetooth beacons, alpha-numeric characters, and any combination thereof.

19. The computerized system of claim 17 wherein the subsequent event record includes a verification data representing that an individual viewed the object indicium and compared it with the digital indicium retrieved from the immutable storage and included in the first event record.

20. The computerized system of claim 12 wherein the set of computer readable instructions include instructions configured for converting the first event record into an encrypted record having a fixed length.

* * * * *

UNITED STATES PATENT AND TRADEMARK OFFICE
CERTIFICATE OF CORRECTION

PATENT NO. : 11,288,308 B2
APPLICATION NO. : 17/176056
DATED : March 29, 2022
INVENTOR(S) : Jeremy Blackburn et al.

It is certified that error appears in the above-identified patent and that said Letters Patent is hereby corrected as shown below:

On the Title Page

Related U.S. Application Data should read as follows:
(63) This application is a continuation in part of application No. 17/176,056 filed 02/15/2021, now Pat. No. 11,288,308 which is a continuation in part of application No. 17/128,084 filed 12/19/2020, now Pat. No. 11,521,157 which is a continuation in part of application No. 16/997,840 filed August 19, 2020, now Pat. No. 11,449,949 which is a continuation in part of application No. 16/994,585 filed August 15, 2020, now Pat. No. 11,232,652 which is a continuation in part of application No. 16/991,916 filed on August 12, 2020, now Pat. No. 11,216,823, which is a continuation in part of application No. 16/876,080, filed May 17, 2020, now Pat. No. 11,423,360 which is a continuation in part of application No. 16/810,782 filed on March 5, 2020, now Pat. No. 11,216,781 which is a continuation in part of application No. 16/510,634 filed on July 12, 2019, now Pat. No. 10,713,737 and application No. 16/510,642 filed on July 12, 2019, now Pat. No. 11,216,772. Application Nos 16/510,642 and 16/510,634 are both continuations in part of application No. 16/452,076 filed June 25, 2019.

Signed and Sealed this
Thirtieth Day of July, 2024

Katherine Kelly Vidal
*Director of the United States Patent and Trademark Office*